(12) United States Patent
Sano et al.

(10) Patent No.: US 12,161,446 B2
(45) Date of Patent: Dec. 10, 2024

(54) SPHYGMOMANOMETER, BLOOD PRESSURE MEASUREMENT METHOD, AND COMPUTER-READABLE RECORDING MEDIUM

(71) Applicants: OMRON HEALTHCARE CO., LTD., Muko (JP); OMRON CORPORATION, Kyoto (JP)

(72) Inventors: Yoshihiko Sano, Kyoto (JP); Takanori Nishioka, Kyoto (JP); Takeshi Kubo, Kyoto (JP); Takehiro Hamaguchi, Kyoto (JP); Yasuo Asano, Kyoto (JP)

(73) Assignees: OMRON HEALTHCARE CO., LTD., Muko (JP); OMRON CORPORATION, Kyoto (JP)

( * ) Notice: Subject to any disclaimer, the term of this patent is extended or adjusted under 35 U.S.C. 154(b) by 769 days.

(21) Appl. No.: 17/413,438

(22) Filed: Jun. 11, 2021

(65) Prior Publication Data
US 2022/0218216 A1    Jul. 14, 2022

Related U.S. Application Data

(63) Continuation of application No. PCT/JP2019/046973, filed on Dec. 2, 2019.

(30) Foreign Application Priority Data

Dec. 27, 2018 (JP) ................. 2018-245724

(51) Int. Cl.
*A61B 5/022* (2006.01)
*A61B 5/021* (2006.01)
*A61B 5/0225* (2006.01)

(52) U.S. Cl.
CPC ...... *A61B 5/02225* (2013.01); *A61B 5/02141* (2013.01); *A61B 5/0225* (2013.01); *A61B 2562/0247* (2013.01)

(58) Field of Classification Search
None
See application file for complete search history.

(56) References Cited

U.S. PATENT DOCUMENTS 6,336,901 B1 * 1/2002 Itonaga ................. A61B 5/681
600/499
2002/0170359 A1 * 11/2002 Yamakoshi ........ A61B 5/02141
73/756

(Continued)

FOREIGN PATENT DOCUMENTS

| JP | S58-92340 A | 6/1983 |
| JP | S60-132539 A | 7/1985 |

(Continued)

OTHER PUBLICATIONS

Feb. 18, 2020 Search Report issued in International Patent Application No. PCT/JP2019/046973.

*Primary Examiner* — Devin B Henson
*Assistant Examiner* — Matthew Eric Ogles
(74) *Attorney, Agent, or Firm* — Oliff PLC

(57) ABSTRACT

The present invention provides a sphygmomanometer that can create, before measuring a blood pressure, a state for making a blood pressure measurement accurate. A sphygmomanometer includes a fluid circuit and a control unit. The control unit has a first preparation processing unit, a second preparation processing unit, and a measurement processing unit which operate in a worn state of the sphygmomanometer. The first preparation processing unit operates a pressing cuff to discharge remaining fluid in a sensing cuff to the atmosphere through the fluid circuit. Then, the second preparation processing unit causes the sensing cuff to store a predetermined amount of pressure transmitting fluid received from a pump through the fluid circuit. Subsequently, the measurement processing unit operates the pressing cuff and calculates the blood pressure by the oscillo- (Continued)

metric method based on pressure of the pressure transmitting fluid stored in the sensing cuff.

12 Claims, 28 Drawing Sheets

(56) References Cited

U.S. PATENT DOCUMENTS

| | | | | |
|---|---|---|---|---|
| 2012/0296223 A1* | 11/2012 | Fujii | ............... | A61B 5/0225 |
| | | | | 600/492 |
| 2013/0190576 A1* | 7/2013 | Matsumura | ......... | A61B 5/0235 |
| | | | | 600/301 |

FOREIGN PATENT DOCUMENTS

| JP | S61-284229 A | 12/1986 |
|---|---|---|
| JP | S63-50304 U | 4/1988 |
| JP | 2018-102867 A | 7/2018 |

* cited by examiner ized in this specification a sphygmomanometer, blood pressure measurement method, and computer-readable recording medium.

SPHYGMOMANOMETER, BLOOD PRESSURE MEASUREMENT METHOD, AND COMPUTER-READABLE RECORDING MEDIUM

CROSS-REFERENCE TO RELATED APPLICATION

This application is based on an application No. 2018-245724 filed in Japan on Dec. 27, 2018, the entire content of which is hereby incorporated by reference.

TECHNICAL FIELD

The present invention relates to a sphygmomanometer, a blood pressure measurement method, and a program, and more particularly, to a sphygmomanometer to be worn around a measurement target site in its circumferential direction, a blood pressure measurement method using the sphygmomanometer, and a computer-readable recording medium storing a program for causing a computer to execute such a blood pressure measurement.

BACKGROUND ART

Conventionally, as a sphygmomanometer of this type, for example, there is one disclosed in Patent Literature 1 (JP 2018-102867 A). The sphygmomanometer has a cuff that is wrapped around a wrist and a main body that is integrally provided with the cuff. The sphygmomanometer is provided with, on an inner side of a band-shaped belt, a bag-shaped sensing cuff that presses an artery, an intervening member provided on an outer side of the sensing cuff, and a bag-shaped pressing cuff provided on an outer side of the intervening member. The main body of the sphygmomanometer includes a pump, an exhaust valve mounted on the pump and configured to be closed or opened according to on/off of the pump, a pressure sensor, a first flow path that fluid-flowably connects the pump with the pressing cuff, and a second flow path that fluid-flowably connects the pump or the first flow path with the sensing cuff and has an on-off valve inserted therein. When the blood pressure is measured using the sphygmomanometer, first, the exhaust valve and the on-off valve are opened, and both the pressing cuff and the sensing cuff are opened to the atmospheric pressure. Next, with the exhaust valve closed and the on-off valve opened, air supply from the pump to the pressing cuff and the sensing cuff is started. When a predetermined amount of air is supplied to the sensing cuff, the on-off valve is closed to seal the sensing cuff. After that, the air supply from the pump to the pressing cuff is continued, and the wrist is compressed by the pressing cuff through the sensing cuff. Then, the blood pressure is calculated by the oscillometric method based on pressure of the air (measured by the pressure sensor) stored in the sensing cuff.

SUMMARY OF INVENTION

Incidentally, after the blood pressure measurement by the sphygmomanometer and before the next blood pressure measurement, when both the pressing cuff and the sensing cuff are opened to the atmospheric pressure, the air remains in the sensing cuff. Moreover, a remaining amount of the air in the sensing cuff may differ each time depending on a wrapping state (loose or tight) of the belt. The inventors have found that this difference in the remaining amount of the air adversely affects accuracy of blood pressure measurement.

Therefore, an object of the present invention is to provide a sphygmomanometer, and a blood pressure measurement method, which can create, before measuring a blood pressure, a state for making a blood pressure measurement accurate. In addition, an object of the present invention is to provide a computer-readable recording medium storing a program for causing a computer to execute such a blood pressure measurement.

In order to achieve the above object, a sphygmomanometer according to the present disclosure is a sphygmomanometer comprising:

a main body mounted with a pump;
a belt extending from the main body and worn around a measurement target site;
a sensing cuff arranged, in a worn state of the belt being worn around the measurement target site, at a portion of an inner circumferential side of the belt that crosses an artery passing portion of the measurement target site, and configured in a bag shape so as to allow storage of a pressure transmitting fluid;
a pressing member that presses the sensing cuff toward the measurement target site and causes the sensing cuff to compress the measurement target site;
a fluid circuit that can be configured by switching among a supply mode of suppling the pressure transmitting fluid from the pump to the sensing cuff, a discharge mode of discharging the fluid from the sensing cuff to atmosphere, and a shut-off mode of shutting off fluid supply to the sensing cuff and fluid discharge from the sensing cuff; and
a control unit, wherein,
the control unit includes, in the worn state:
a first preparation processing unit that, with the fluid circuit switched to the discharge mode, operates the pressing member to press the sensing cuff toward the measurement target site and discharges a fluid remaining in the sensing cuff to the atmosphere through the fluid circuit;
a second preparation processing unit that, with the fluid circuit switched to the supply mode after operation of the first preparation processing unit, causes the sensing cuff to store a predetermined amount of the pressure transmitting fluid received from the pump through the fluid circuit; and
a measurement processing unit that, with the fluid circuit switched to the shut-off mode after operation of the second preparation processing unit, operates the pressing member to press the sensing cuff toward the measurement target site and causes the sensing cuff to compress the measurement target site, and meanwhile, calculates a blood pressure of the measurement target site based on a pressure of the pressure transmitting fluid stored in the sensing cuff by an oscillometric method.

The "fluid" is typically air, but may be other gas or liquid.
The "inner circumferential side" of the belt refers to a side facing the measurement target site in the worn state wrapped around the measurement target site.

In another aspect, a blood pressure measurement method according to the present disclosure is a blood pressure measurement method that uses a sphygmomanometer comprising: a main body mounted with a pump; a belt extending from the main body and worn around a measurement target site; a sensing cuff arranged, in a worn state of the belt being worn around the measurement target site, at a portion of an inner circumferential side of the belt that crosses an artery passing portion of the measurement target site, and configured in a bag shape so as to allow storage of a pressure transmitting fluid; a pressing member that presses the sensing cuff toward the measurement target site and causes the sensing cuff to compress the measurement target site; and a fluid circuit that can be configured by switching among a supply mode of suppling the pressure transmitting fluid from the pump to the sensing cuff, a discharge mode of discharging the fluid from the sensing cuff to atmosphere, and a shut-off mode of shutting off fluid supply to the sensing cuff and fluid discharge from the sensing cuff, wherein, the method comprising, in the worn state:
executing first preparation processing that, with the fluid circuit switched to the discharge mode, operates the pressing member to press the sensing cuff toward the measurement target site and discharges a fluid remaining in the sensing cuff to the atmosphere through the fluid circuit;
executing second preparation processing that, with the fluid circuit switched to the supply mode after the first preparation processing, causes the sensing cuff to store a predetermined amount of the pressure transmitting fluid received from the pump through the fluid circuit; and
executing measurement processing that, with the fluid circuit switched to the shut-off mode after the second preparation processing, operates the pressing member to press the sensing cuff toward the measurement target site and causes the sensing cuff to compress the measurement target site, and meanwhile, calculates a blood pressure of the measurement target site based on a pressure of the pressure transmitting fluid stored in the sensing cuff by an oscillometric method.

In yet another aspect, a computer-readable recording medium storing a program according to the present disclosure is a computer-readable recording medium non-transitorily storing a program for causing a computer to execute the above blood pressure measurement method.

BRIEF DESCRIPTION OF DRAWINGS

The present invention will become more fully understood from the detailed description given hereinbelow and the accompanying drawings which are given by way of illustration only, and thus are not limitative of the present invention, and wherein.

DESCRIPTION OF EMBODIMENTS

Hereinafter, embodiments of the present invention is described in detail with reference to the drawings.

First Embodiment

Configuration of Sphygmomanometer According to First Embodiment

Figure 1:
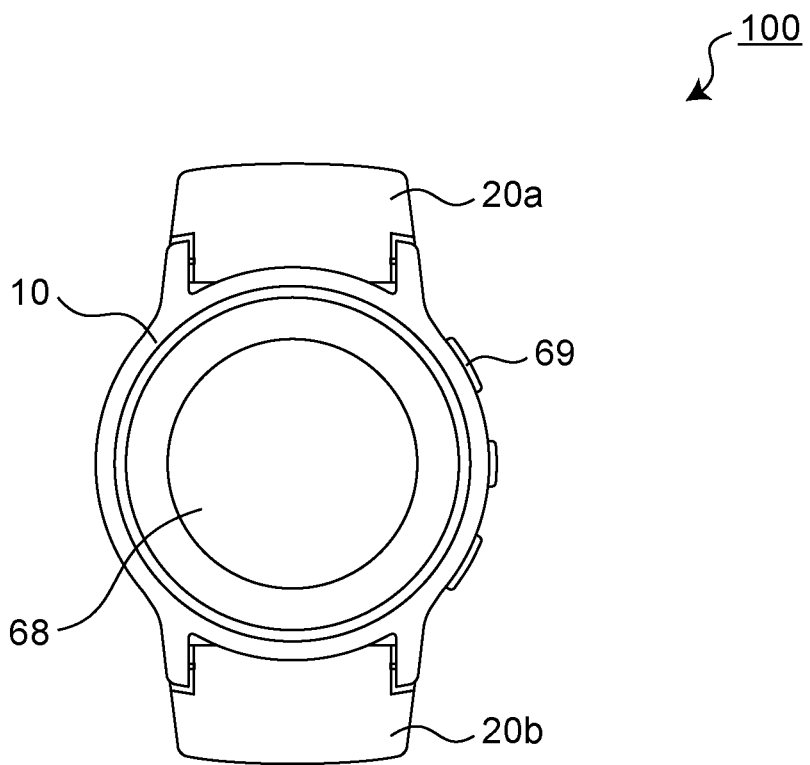
FIG. 1 is a front view showing a schematic external configuration of a sphygmomanometer according to first and second embodiments.
Figure 2:
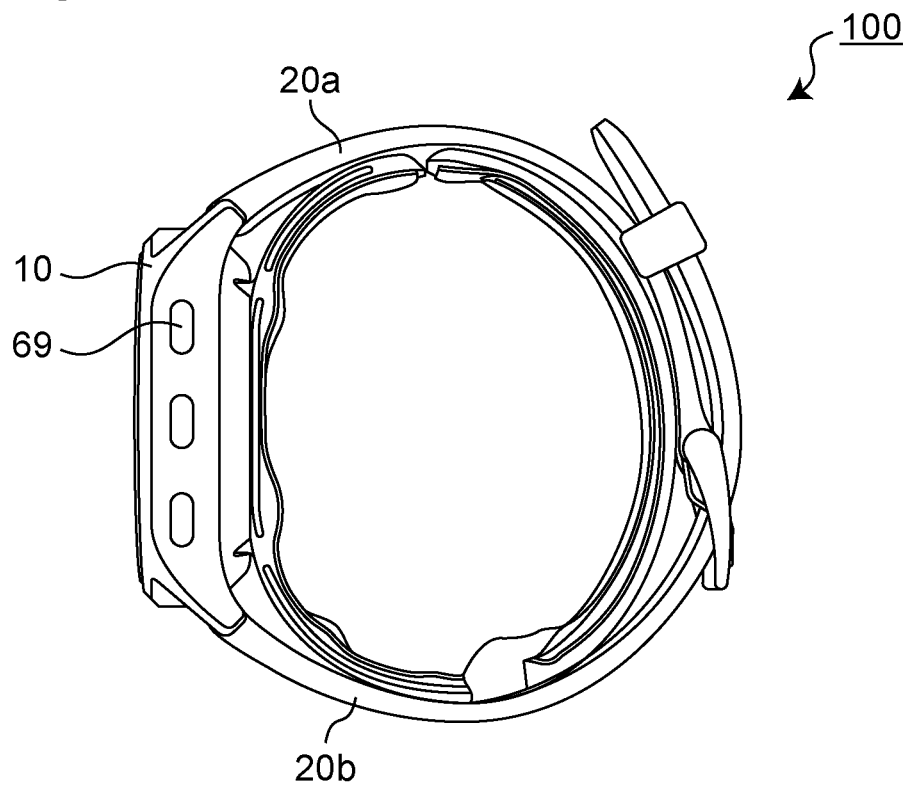
FIG. 2 is a side view showing a schematic external configuration of the sphygmomanometer according to the first and second embodiments.
Figure 3:
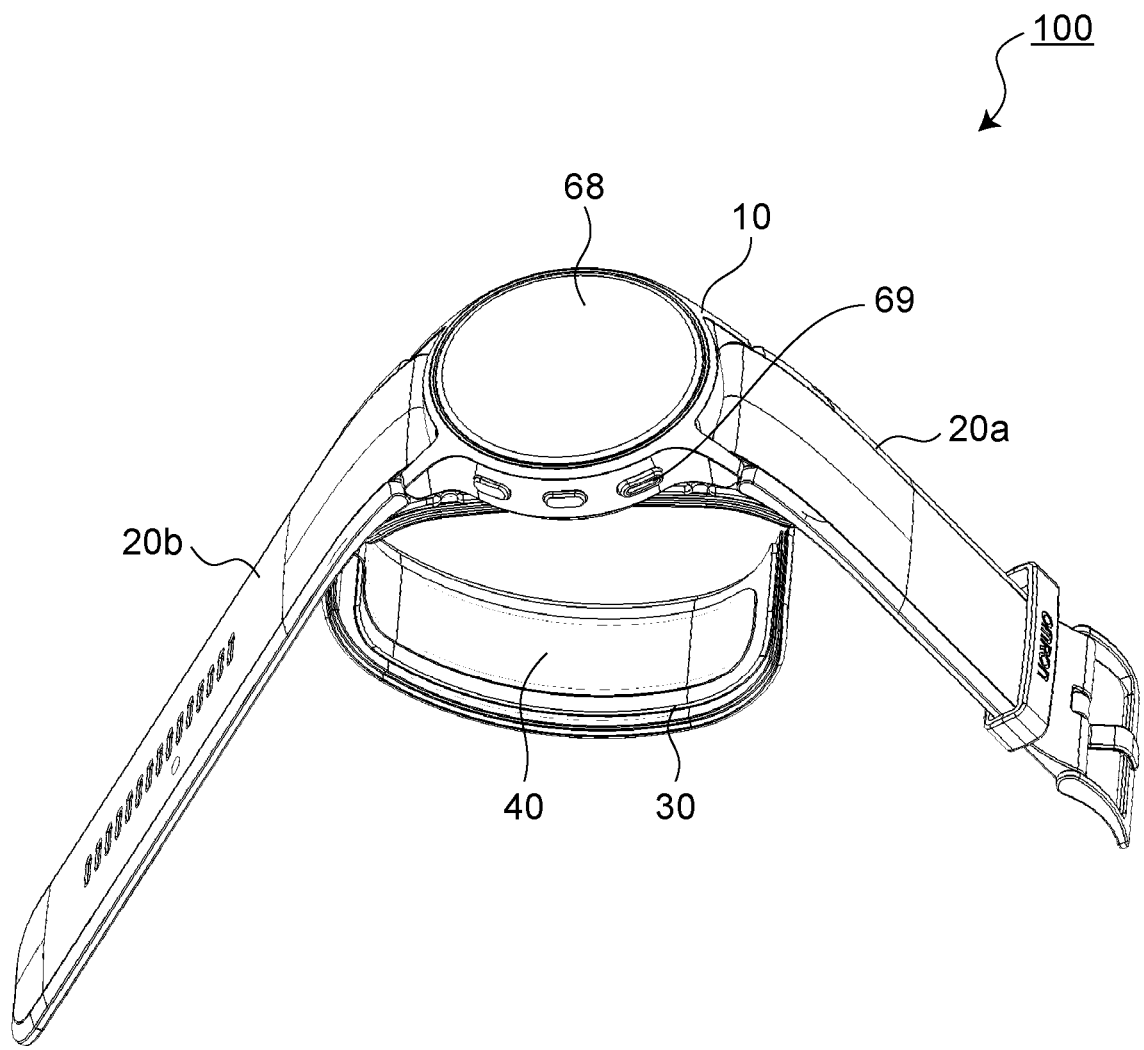
FIG. 3 is a perspective view showing a schematic external configuration of the sphygmomanometer according to the first embodiment.

FIG. 1 shows a configuration in which a sphygmomanometer 100 according to the present embodiment is viewed from the front. FIG. 2 shows the configuration of the sphygmomanometer 100 as viewed from the side. Further, FIG. 3 shows the configuration of the sphygmomanometer 100 viewed from an oblique direction with the belt described later opened. The schematic external configuration of the sphygmomanometer 100 is described with reference to FIGS. 1 to 3.

The sphygmomanometer 100 mainly includes a main body 10, two belts 20a and 20b, a pressing cuff 30 constituting a pressing member shown in FIG. 3, and a sensing cuff 40.

As shown in FIGS. 1 to 3, the main body 10 includes a display device 68 and an operation device 69 constituted of a plurality of buttons. Further, the main body 10 is mounted with a pump described later. Further, the one belt 20a and the other belt 20b are attached to the main body 10. The two belts 20a and 20b extend from the main body 10 and are worn around the measurement target site. By fastening the one belt 20a and the other belt 20b, a state in which the sphygmomanometer 100 is worn on the measurement target site (see FIG. 4, which is referred to as a "worn state") is created.

Further, in the present embodiment, the cuffs 30 and 40 constitute a cuff structure having a stacked structure. In the above worn state of the sphygmomanometer 100, the pressing cuff 30 and the sensing cuff 40 are arranged in this order when viewed from the side of a fastening part 20T of the belts 20a and 20b. The pressing cuff 30 generates a pressing force on the measurement target site. Then, the pressing force is applied to the measurement target site through the sensing cuff 40. As shown in JP 2018-102867 A, the cuff structure may include a curler, a back plate, and others (not shown) in addition to the pressing cuff 30 and the sensing cuff 40 described above. A member including such as the belts 20a and 20b, the curler, the pressing cuff 30, and the back plate functions as a pressing member that generates the pressing force on the measurement target site. The pressing member including the pressing cuff 30 presses the sensing cuff 40 toward the measurement target site, and causes the sensing cuff 40 to compress (press) the measurement target site.

Figure 4:
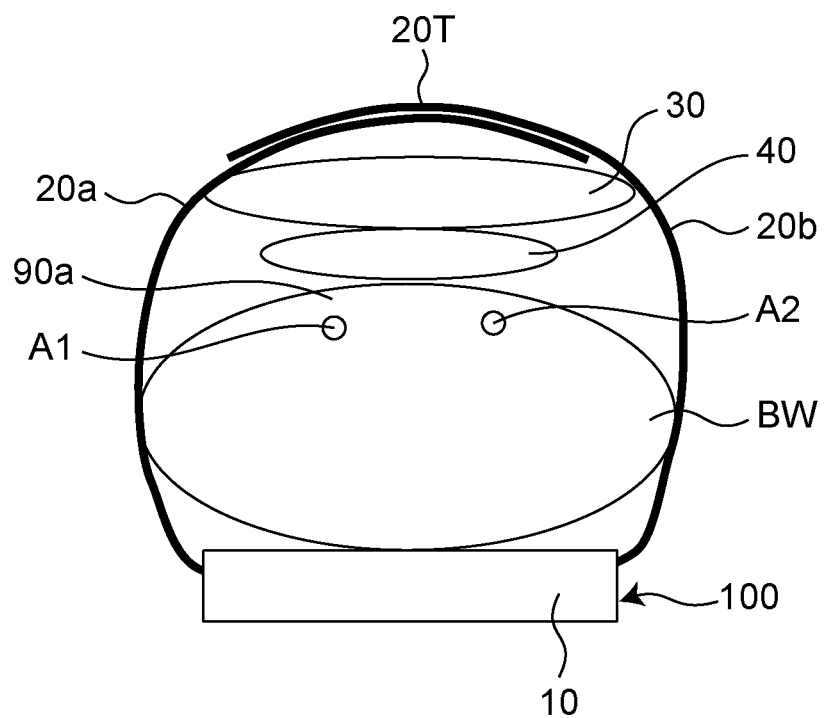
FIG. 4 is a cross-sectional view showing a state in which the sphygmomanometer according to the first embodiment is worn around the wrist.

FIG. 4 shows a cross-sectional view of the sphygmomanometer 100 being worn around a wrist BW being the measurement target site. As shown in FIG. 4, the pressing cuff 30 constituting the pressing member has a bag shape and is arranged between the belts 20a and 20b and the sensing cuff 40. As described above, the belts 20a and 20b are wrapped around the wrist BW in the circumferential direction so that the sphygmomanometer 100 is worn around the wrist BW. In the worn state of the present embodiment, as shown in FIG. 4, the wrist BW, the sensing cuff 40, and the pressing cuff 30 are arranged in this order from the main body 10 toward the fastening part 20T of the belts 20a and 20b. In the configuration example of FIG. 4, the main body 10 is arranged at a portion opposite to the sensing cuff 40 in the circumferential direction of the belts 20a and 20b.

In the above worn state, the bag-shaped pressing cuff 30 extends, for example, along the circumferential direction of the wrist BW. Further, the bag-shaped sensing cuff 40 is arranged on the inner circumferential side of the belts 20a and 20b with respect to the pressing cuff 30 and is in contact with the wrist BW (indirectly or directly), and extends in the circumferential direction so as to cross an artery passing portion 90a of the wrist BW. The "inner circumference side" of the belts 20a and 20b refers to the side facing the wrist BW in the worn state of wrapping around the wrist BW.

In FIG. 4, a radial artery A1 and an ulnar artery A2 of the wrist BW are shown. In the present embodiment, the pressing cuff 30 constituting the pressing member is arranged between the belts 20a, 20b and the sensing cuff 40. The pressing cuff 30 presses the sensing cuff 40 toward the wrist BW, causing the sensing cuff 40 to press the wrist BW. Details of a specific example of the sphygmomanometer 100 and an example of wearing the sphygmomanometer 100 are described in JP 2018-102867 A.

Figure 5:
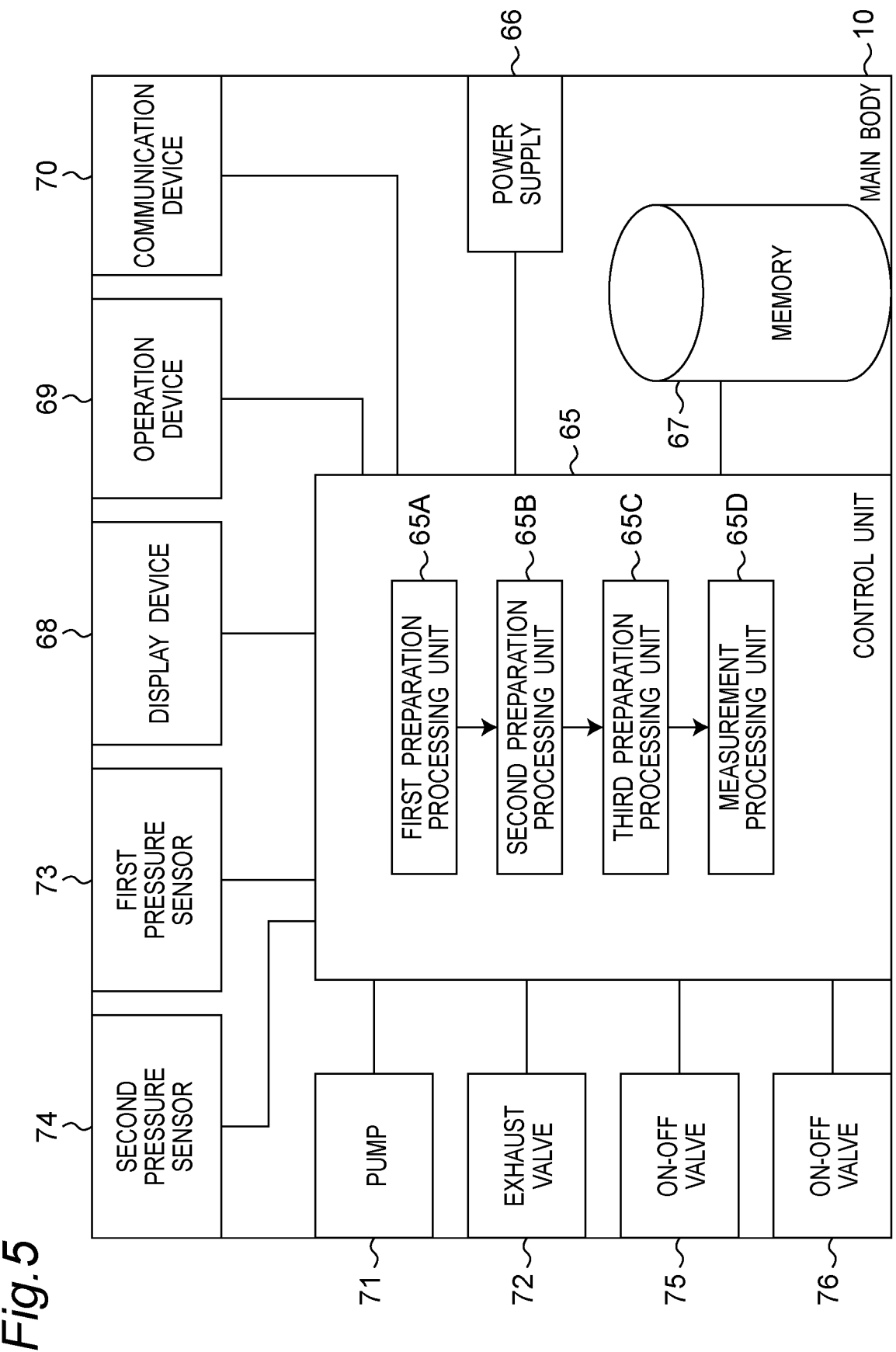
FIG. 5 is a diagram showing a schematic configuration of a control system of the sphygmomanometer according to the first embodiment.

FIG. 5 shows a schematic configuration of a control system of the sphygmomanometer 100. As shown in FIG. 5, the main body 10 of the sphygmomanometer 100 includes a control unit 65 that is responsible for control, and a plurality of control target constituents 66 to 76 that are controlled by the control unit 65. Here, the plurality of control target constituents include a power supply 66, a memory 67, a display device 68, an operation device 69, a communication device 70, a pump 71, an exhaust valve 72, a first pressure sensor (pressing cuff pressure sensor) 73, and a second pressure sensor (sensing cuff pressure sensor) 74, and two on-off valves 75 and 76.

The power supply 66 is composed of a rechargeable secondary battery in this example. The power supply 66 supplies driving power to the elements mounted on the main body 10, for example, the processor 65, the memory 67, the display device 68, the communication device 70, the pump 71, the exhaust valve 72, each of the pressure sensors 73 and 74, and each of the on-off valves 75 and 76.

The memory 67 stores various types of data. For example, the memory 67 can store the measurement values measured by the sphygmomanometer 100, the measurement results of the pressure sensors 73 and 74, and others. Further, the memory 67 can also store various types of data generated by the control unit 65. The memory 67 includes a random access memory (RAM), a read only memory (ROM), and others. For example, various programs are stored in the memory 67 in a modifiable manner.

The display device 68 is composed of a liquid crystal display (LCD) as an example. The display device 68 displays information related to blood pressure measurement such as a blood pressure measurement result and other information according to a control signal from the control unit 65. The display device 68 may have a function as a touch panel.

The operation device 69 is composed of a plurality of buttons that receive instructions from a user. When the operation device 69 receives an instruction from the user, the operation/motion according to the instruction is performed under the control of the control unit 65. The operation device 69 may be, for example, a pressure-sensitive type (resistive type) or proximity type (capacitance type) touch panel switch. Further, a microphone (not shown) may be provided to receive a voice instruction from the user.

The communication device 70 transmits various types of data and various signals to an external device via a communication network, and receives information from the external device via the communication network. The network may be wireless communication or wired communication.

The pump 71, in this example, is composed of a piezoelectric pump and is driven based on a control signal given by the control unit 65. The pump 71 can supply a pressurizing fluid to the cuffs 30 and 40 through respective flow paths described later. Note that any type of liquid or any type of gas can be adopted as the fluid. In the present embodiment, the fluid is air (hereinafter, the description is made assuming that the fluid is air). The configuration of a flow path system including the pump 71 and other air components 72 to 76 are described later.

The exhaust valve 72 is controlled according to the operation of the pump 71. That is, the opening and closing of the exhaust valve 72 is controlled according to the on/off (supplying air/stop supplying air) of the pump 71. For example, the exhaust valve 72 closes when the pump 71 is turned on. On the other hand, the exhaust valve 72 opens when the pump 71 is turned off. In the open state of the exhaust valve 72, for example, the air in the sensing cuff 40 can be discharged to the atmosphere through a flow path described later. The exhaust valve 72 has a function of a check valve, and the discharged air does not flow back.

The first pressure sensor 73 and the second pressure sensor 74 include, for example, a piezoresistive pressure sensor. The first pressure sensor 73 detects the pressure in the pressing cuff 30 through a flow path described later. The second pressure sensor 74 detects the pressure in the sensing cuff 40 through a flow path described later.

The on-off valves 75 and 76 are respectively inserted into the flow paths described later. The opening and closing (opening degree) of the on-off valves 75 and 76 is controlled based on the control signal given from the control unit 65. In the open state of the on-off valves 75 and 76, the air flows through the on-off valves 75 and 76. On the other hand, in the close state of the on-off valves 75 and 76, the air does not flow through the on-off valves 75 and 76.

The control unit 65 includes a central processing unit (CPU) in this example. For example, the control unit 65 reads each program and each piece of data stored in the memory 67. Further, the control unit 65 controls each of the constituents 67 to 76 according to the read program to execute a predetermined operation (function). Further, the control unit 65 performs a predetermined calculation, analysis, processing, and so on, in the control unit 65 according to the read program. It should be noted that a part or all of each function executed by the control unit 65 may be configured in hardware by one or a plurality of integrated circuits or the like.

As shown in FIG. 5, the control unit 65 according to the present embodiment includes a first preparation processing unit 65A, a second preparation processing unit 65B, a third preparation processing unit 65C, and a measurement processing unit 65D as functional blocks. The operations of the blocks 65A to 65D are described in detail in the description of the operations described later.

Figure 6:
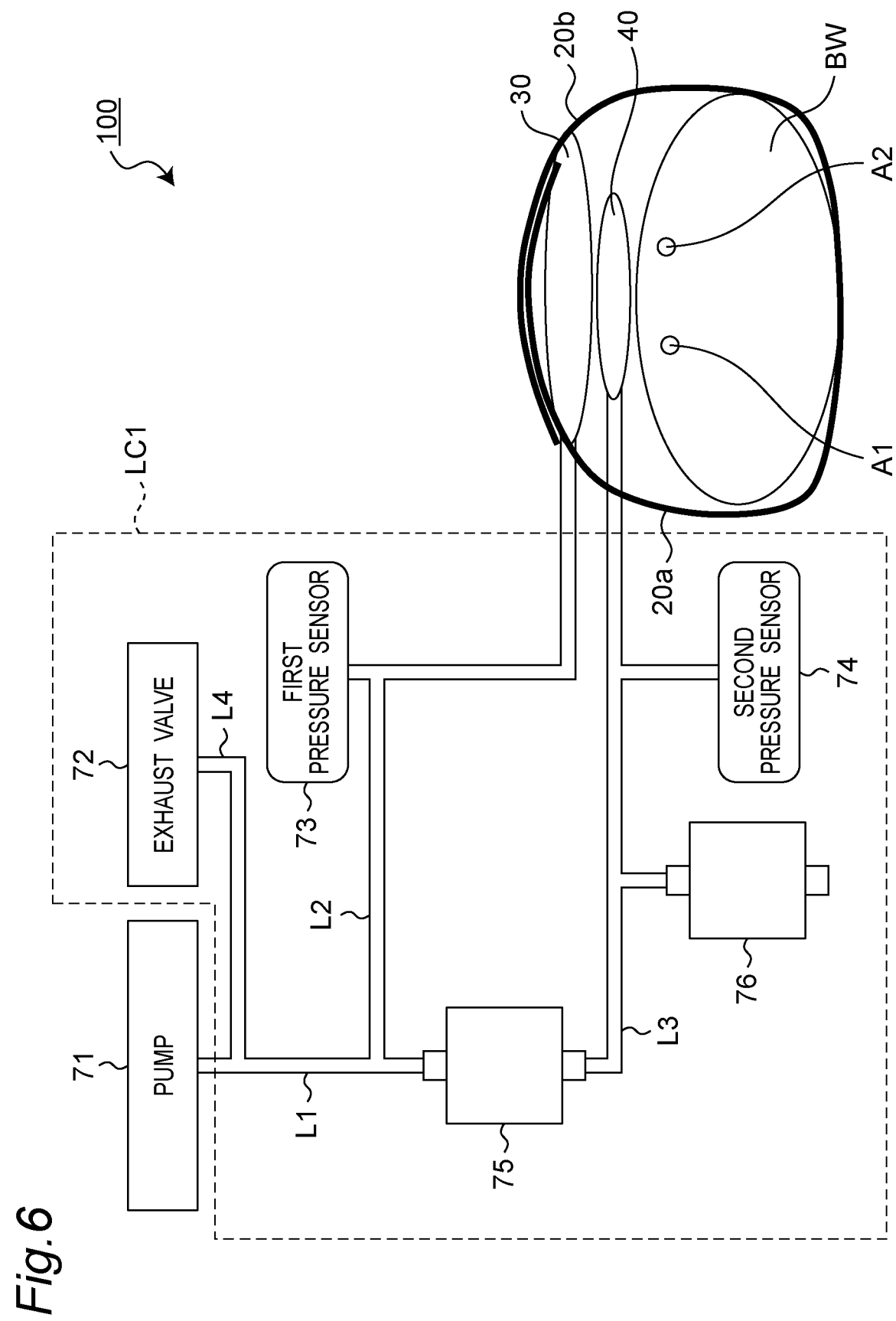
FIG. 6 is a diagram showing a schematic configuration of a flow path system of the sphygmomanometer according to the first embodiment.

FIG. 6 shows a schematic configuration of the flow path system of the sphygmomanometer 100. The sphygmomanometer 100 shown in FIG. 6 includes the pump 71, a fluid circuit LC1, the pressing cuff 30, and the sensing cuff 40. Actually, the pump 71 and the fluid circuit LC1 are mounted on the main body 10 (see FIG. 4). However, in FIG. 6, the flow path system is developed and shown for easy understanding.

The fluid circuit LC1 can be configured by switching between a supply mode PM, a discharge mode DM, and a shut-off mode SM. Note that the supply mode PM is a mode for supplying pressure transmitting air from the pump 71 to the sensing cuff 40. The discharge mode DM is a mode for discharging the air from the sensing cuff 40 to the atmosphere. The shut-off mode SM is a mode for blocking the air supply to the sensing cuff 40 and the air discharge from the sensing cuff 40. Further, the fluid circuit LC1 is configured to operate (expand) the pressing cuff 30 forming the pressing member, or deactivate the same (exhaust air from the pressing cuff 30).

Specifically, the fluid circuit LC1 according to the present embodiment includes the exhaust valve 72, each of the on-off valves 75 and 76, each of the pressure sensors 73 and 74, and each of flow paths L1 to L4. Here, the air flows in each of the flow paths L1 to L4.

As shown in FIG. 6, the flow path L1 connects the pump 71 and the on-off valve 75. The flow path L2 connects the flow path L1 and the pressing cuff 30. The flow path L3 connects the on-off valve 75 and the sensing cuff 40. Further, the flow path L4 connects the exhaust valve 72 and the flow path L1. The on-off valve 75 is inserted between the flow path L1 and the flow path L3. The first pressure sensor 73 is connected to the flow path L2. The second pressure sensor 74 is connected to the flow path L3. Further, the on-off valve 76 is inserted between the flow path L3 and the atmosphere.

Operation of Sphygmomanometer According to the First Embodiment

Figure 7:
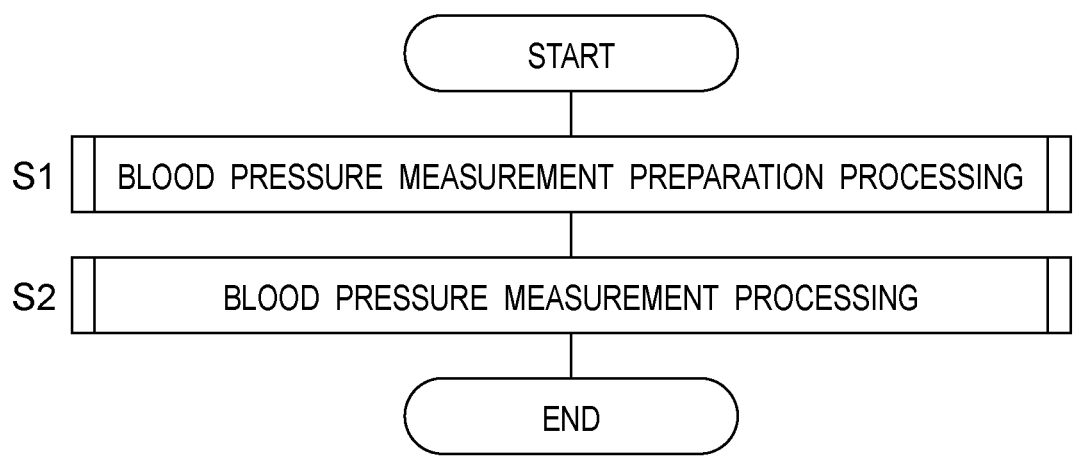
FIG. 7 is a schematic flowchart showing a flow of operation of the sphygmomanometer according to the first and second embodiments.

FIG. 7 shows a flow of the blood pressure measurement method using the sphygmomanometer 100 according to the present embodiment. After the sphygmomanometer 100 is worn around the wrist BW, as shown in FIG. 7, blood pressure measurement preparation processing is performed in step S1, and blood pressure measurement processing (step S2) is performed after step S1.

(Operation of Blood Pressure Measurement Preparation Processing)

Figure 8:
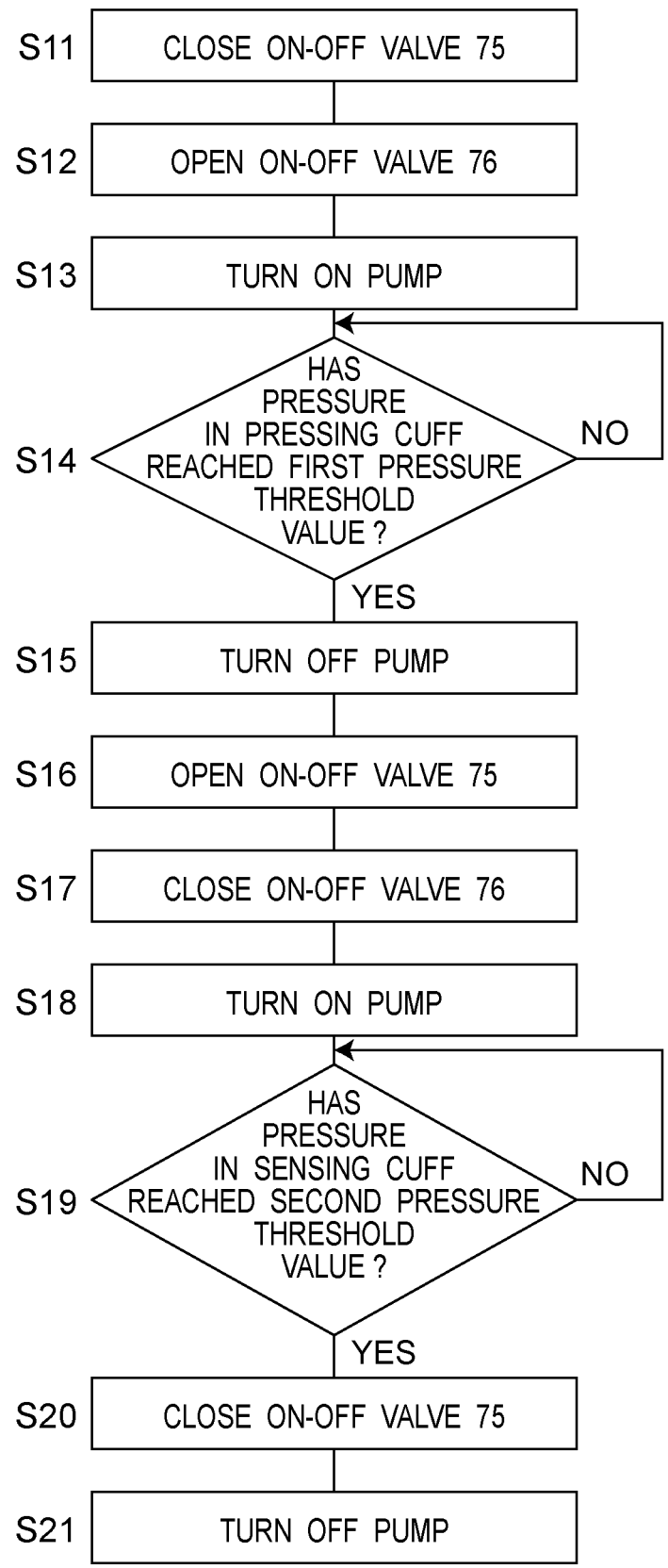
FIG. 8 is a flowchart showing an operation of blood pressure measurement preparation processing in the sphygmomanometer according to the first embodiment.

First, the details of the blood pressure measurement preparation processing in step S1 is described. FIG. 8 shows a specific flow of the blood pressure measurement preparation processing according to the present embodiment.

(1) First, in the state of the sphygmomanometer 100 being worn around the wrist BW, and with the fluid circuit LC1 switched to the discharge mode DM, the first preparation processing unit 65A of the control unit 65 operates (expands) the pressing cuff 30 to press the sensing cuff 40 toward the wrist BW. Then, by the pressing, the air remaining in the sensing cuff 40 is discharged to the atmosphere through the fluid circuit LC1. More specific description is as follows.

Figure 9:
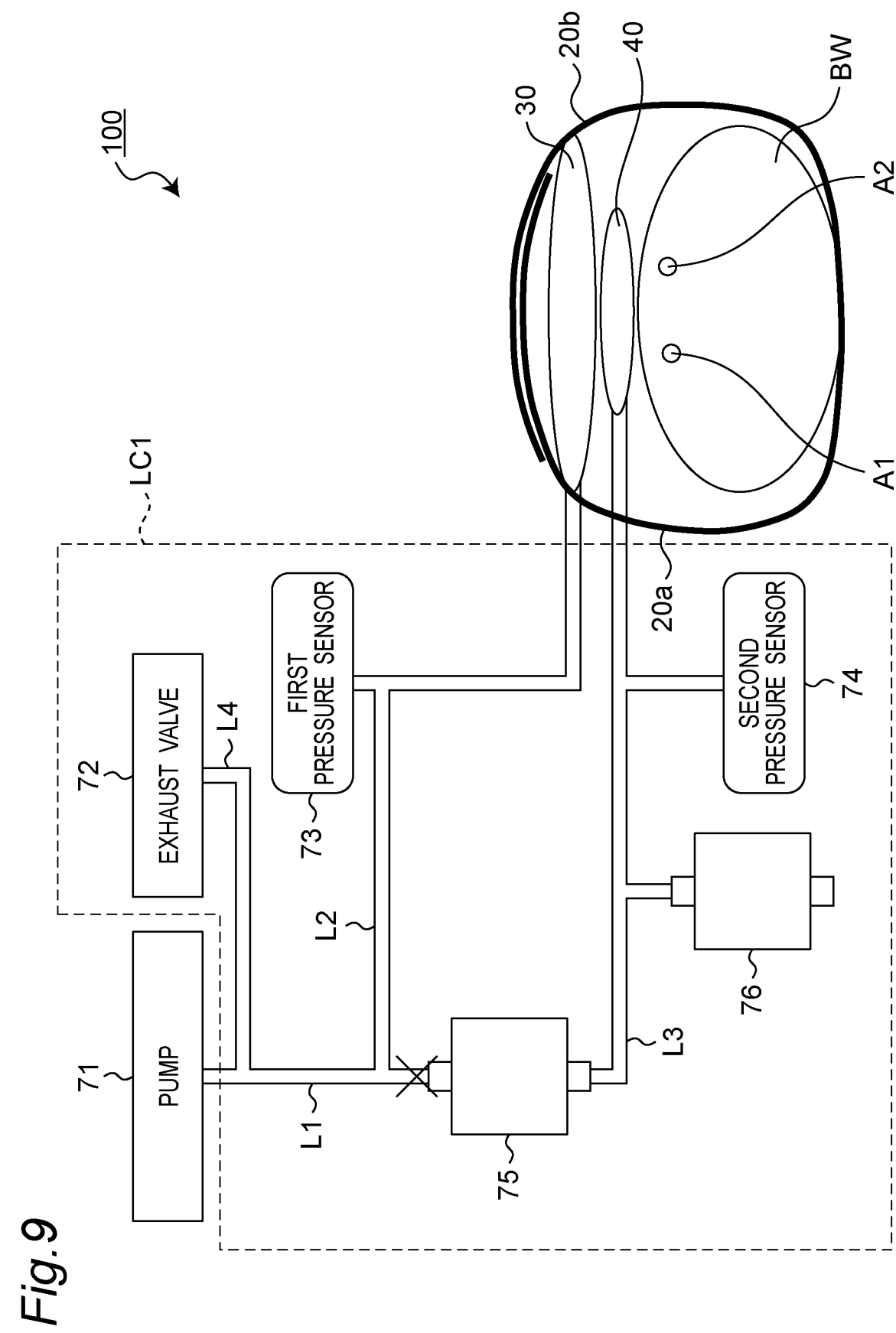
FIG. 9 is a diagram illustrating an operation of the blood pressure measurement preparation processing in the sphygmomanometer according to the first embodiment.

First, in step S11 of FIG. 8, the first preparation processing unit 65A closes the on-off valve 75 (see the "x" mark of the on-off valve 75 in FIG. 9). Further, in step S12, the first preparation processing unit 65A opens the on-off valve 76. By the first preparation processing unit 65A turning the on-off valve 76 to the open state, the first preparation processing unit 65A switches the fluid circuit LC1 to the discharge mode DM.

Next, in step S13, the first preparation processing unit 65A turns the pump 71 to the ON state. As a result, as shown by arrows W1 in FIG. 10, the pump 71 can supply the air to the pressing cuff 30 through the flow paths L1 and L2. By the supply of air in step S13, the pressing cuff 30 is filled with air, and the pressing cuff 30 expands (which can be grasped as the operation of the pressing cuff 30). Then, the expansion of the pressing cuff 30 presses the sensing cuff 40 toward the wrist BW. Then, by the pressing, the air remaining in the sensing cuff 40 is discharged to the atmosphere through the flow path L3 and the on-off valve 76 as shown by arrows W2 in FIG. 10. As described above, in step S13, the expansion of the pressing cuff 30 (the pressing force from the pressing cuff 30) is used to forcibly discharge an amount of air in the sensing cuff 40 from the sensing cuff 40 to the atmosphere, and thereby, an amount of remaining air in the sensing cuff 40 is brought close to zero.

Next, in step S14, the first preparation processing unit 65A determines whether or not the measurement result (pressure in the pressing cuff 30) of the first pressure sensor 73 has reached a first pressure threshold value Pth1. Note that any value can be adopted for the first pressure threshold value Pth1. However, it is desirable that the first pressure threshold value Pth1 is selected from the viewpoint that the remaining air in the sensing cuff 40 can be substantially pushed out by the expansion of the pressing cuff 30. For example, as an example, 30 mmHg is adopted as the first pressure threshold value Pth1.

If the measurement result of the first pressure sensor 73 is less than the first pressure threshold value Pth1 (NO in step S14), the air supply from the pump 71 to the pressing cuff 30 is continued, while the determination processing in step S14 is also continued. On the other hand, if the measurement result of the first pressure sensor 73 has reached the first pressure threshold value Pth1 (YES in step S14), the first preparation processing unit 65A turns the pump 71 to the OFF state (Step S15). As a result, the supply of air from the pump 71 to the pressing cuff 30 is stopped.

Additionally, as described above, the opening and closing of the exhaust valve 72 is controlled in conjunction with the ON/OFF of the pump 71. Specifically, when the pump 71 is in the ON state, the exhaust valve 72 is in the close state, and when the pump 71 is in the OFF state, the exhaust valve 72 is in the open state. Therefore, in step S15, as the pump 71 is turned to the OFF state, the exhaust valve 72 is turned to the open state. Therefore, as shown by arrows W3 in FIG. 11, the air in the pressing cuff 30 is discharged to the atmosphere through the flow paths L2, L1, L4 and the exhaust valve 72.

(2) After the operation of the first preparation processing unit 65A of the control unit 65, and with the fluid circuit LC1 switched to the supply mode PM, the second preparation processing unit 65B of the control unit 65 causes the sensing cuff 40 to store a predetermined amount (appropriate amount) of the pressure transmitting air received from the pump 71 through the fluid circuit LC1. More specific description is as follows.

Figure 12:
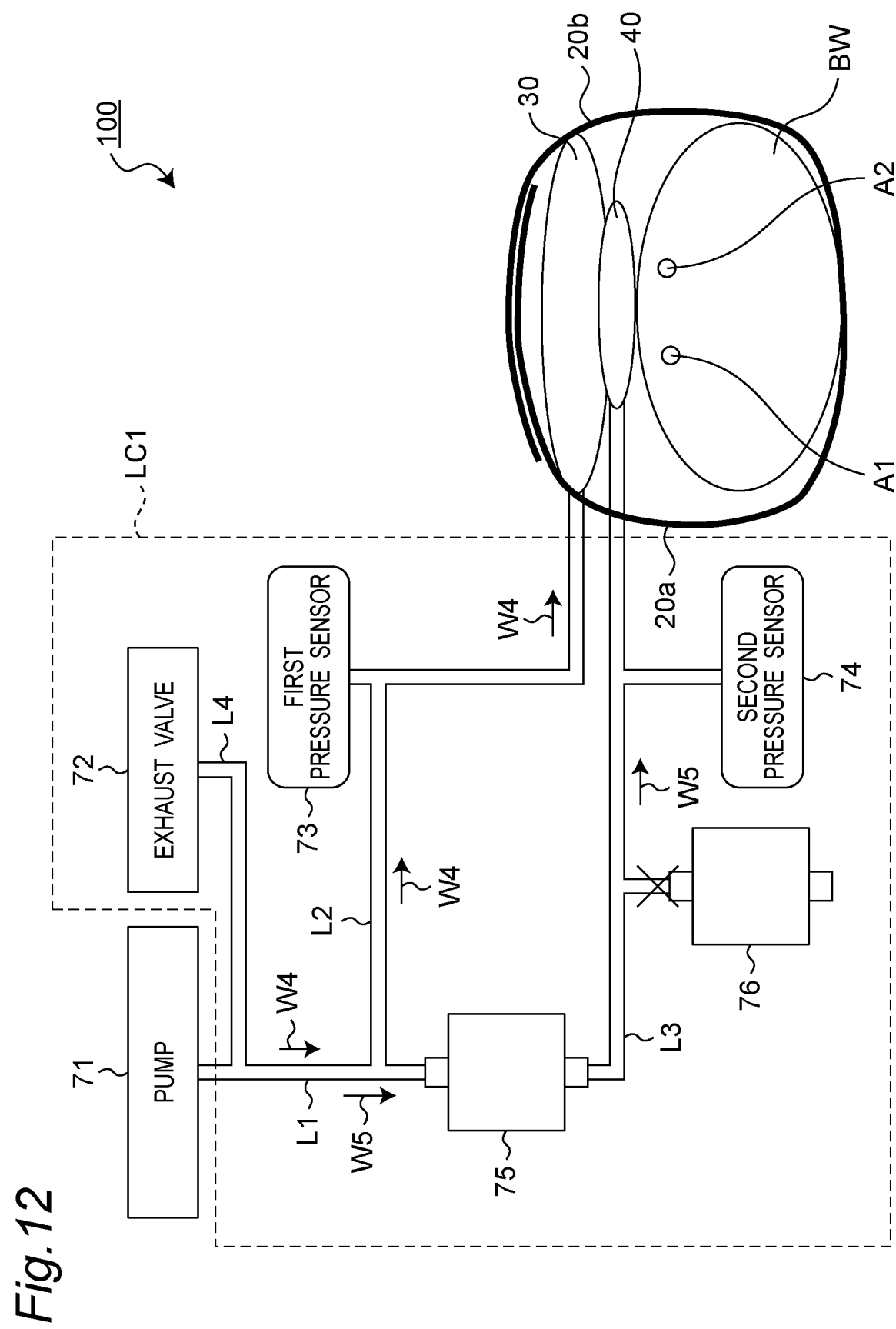
FIG. 12 is a diagram illustrating an operation of the blood pressure measurement preparation processing in the sphygmomanometer according to the first embodiment.

First, in step S16 of FIG. 8, the second preparation processing unit 65B turns the on-off valve 75 to the open state. Next, in step S17, the second preparation processing unit 65B closes the on-off valve 76 (see the "x" mark of the on-off valve 76 in FIG. 12). By the second preparation processing unit 65B opening the on-off valve 75 and closing the on-off valve 76, the second preparation processing unit 65B switches the fluid circuit LC1 to the supply mode PM.

Next, in step S18, the second preparation processing unit 65B turns the pump 71 to the ON state. As a result, as shown by arrows W4 in FIG. 12, the pump 71 can supply air to the pressing cuff 30 through the flow paths L1 and L2, and further, as shown by arrows W5, can supply air (which can be grasped as the appropriate amount of pressure transmitting fluid) to the sensing cuff 40 through the flow path L1, the on-off valve 75, and the flow path L3. By the supply of air in step S18, the pressing cuff 30 is filled with air, and the pressing cuff 30 expands (see FIG. 12). Further, by supplying the air in step S18, the sensing cuff 40 is caused to store an appropriate amount of pressure transmitting fluid (see FIG. 12). Note that an amount of the "appropriate amount" is described in, for example, JP 2018-102867 A.

Next, in step S19, the second preparation processing unit 65B determines whether or not the measurement result (pressure in the sensing cuff 40) of the second pressure sensor 74 has reached a second pressure threshold value Pth2. Note that any value can be adopted for the second pressure threshold value Pth2. For example, as the second pressure threshold value Pth2, less than 40 mmHg (preferably 30 mmHg) is adopted.

If the measurement result of the second pressure sensor 74 is less than the second pressure threshold value Pth2 (NO in step S19), the air supply from the pump 71 to the pressing cuff 30 and to the sensing cuff 40 is continued, while the determination processing in step S19 is also continued.

(3) On the other hand, if the measurement result of the second pressure sensor 74 has reached the second pressure threshold value Pth2 (YES in step S19), after the operation of the second preparation processing unit 65B, the third preparation processing unit 65C of the control unit 65 performs the following control before the blood pressure measurement.

Figure 13:
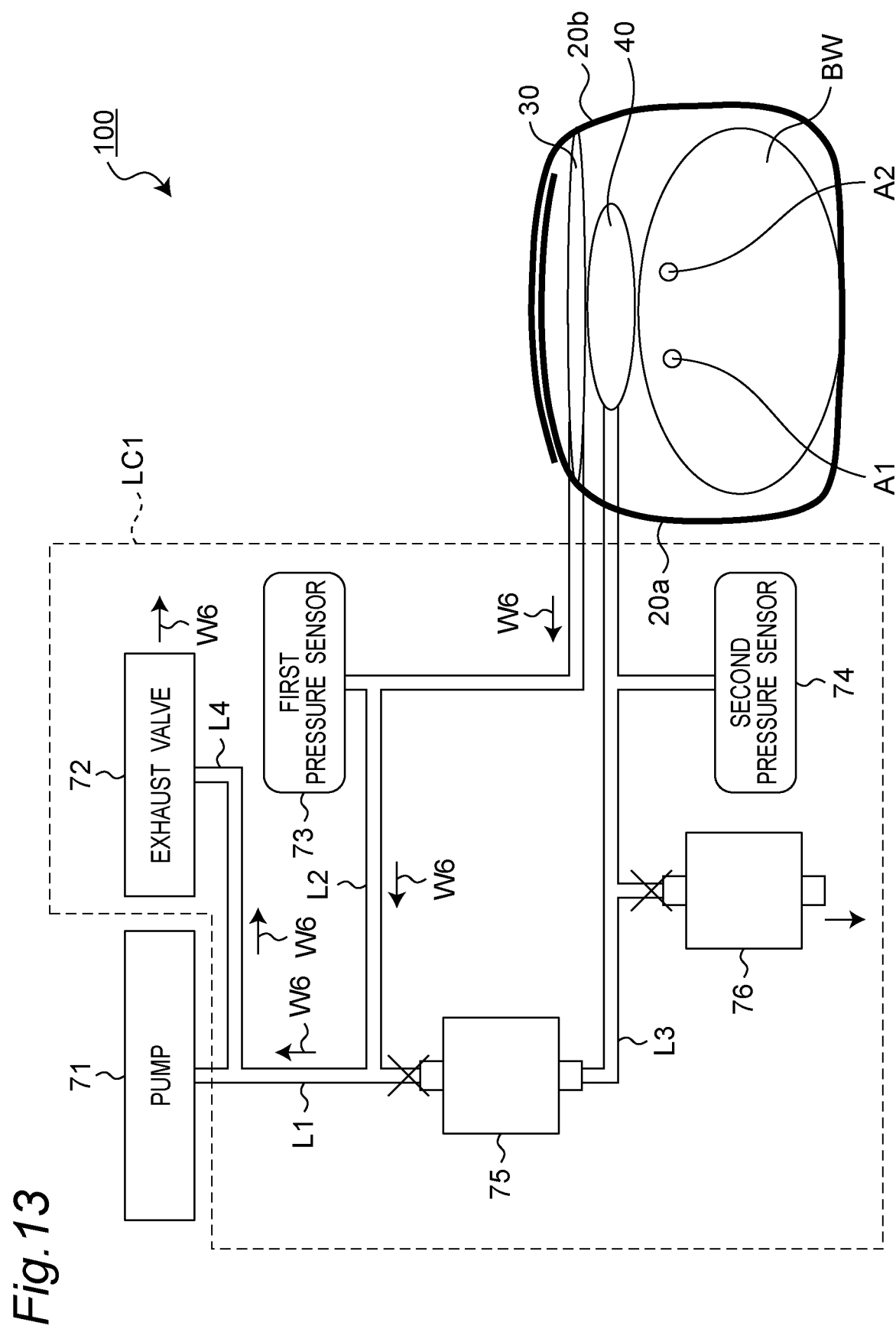
FIG. 13 is a diagram illustrating an operation of the blood pressure measurement preparation processing in the sphygmomanometer according to the first embodiment.

Specifically, in step S20 of FIG. 8, the third preparation processing unit 65C closes the on-off valve 75 (see the "x" mark of the on-off valve 75 in FIG. 13). As shown in FIG. 13, after step S13, the on-off valves 75 and 76 are in the close state (which can be grasped as the switching to the shut-off mode SM of the fluid circuit LC1).

Next, in step S21, the third preparation processing unit 65C turns the pump 71 to the OFF state. As a result, the supply of air from the pump 71 to the pressing cuff 30 is stopped (which can be grasped as the non-operation of the pressing cuff 30). According to the step S21, as shown by arrows W6 in FIG. 13, the air in the pressing cuff 30 which is not operating, is discharged to the atmosphere through the fluid circuit LC1 (flow paths L2, L1, and L4 and exhaust valve 72) which is in the shut-off mode SM. The above is the blood pressure measurement preparation processing (steps S1 in FIG. 7, and FIG. 8) executed by each of the preparation processing units 65A to 65C of the control unit 65.

Figure 10:
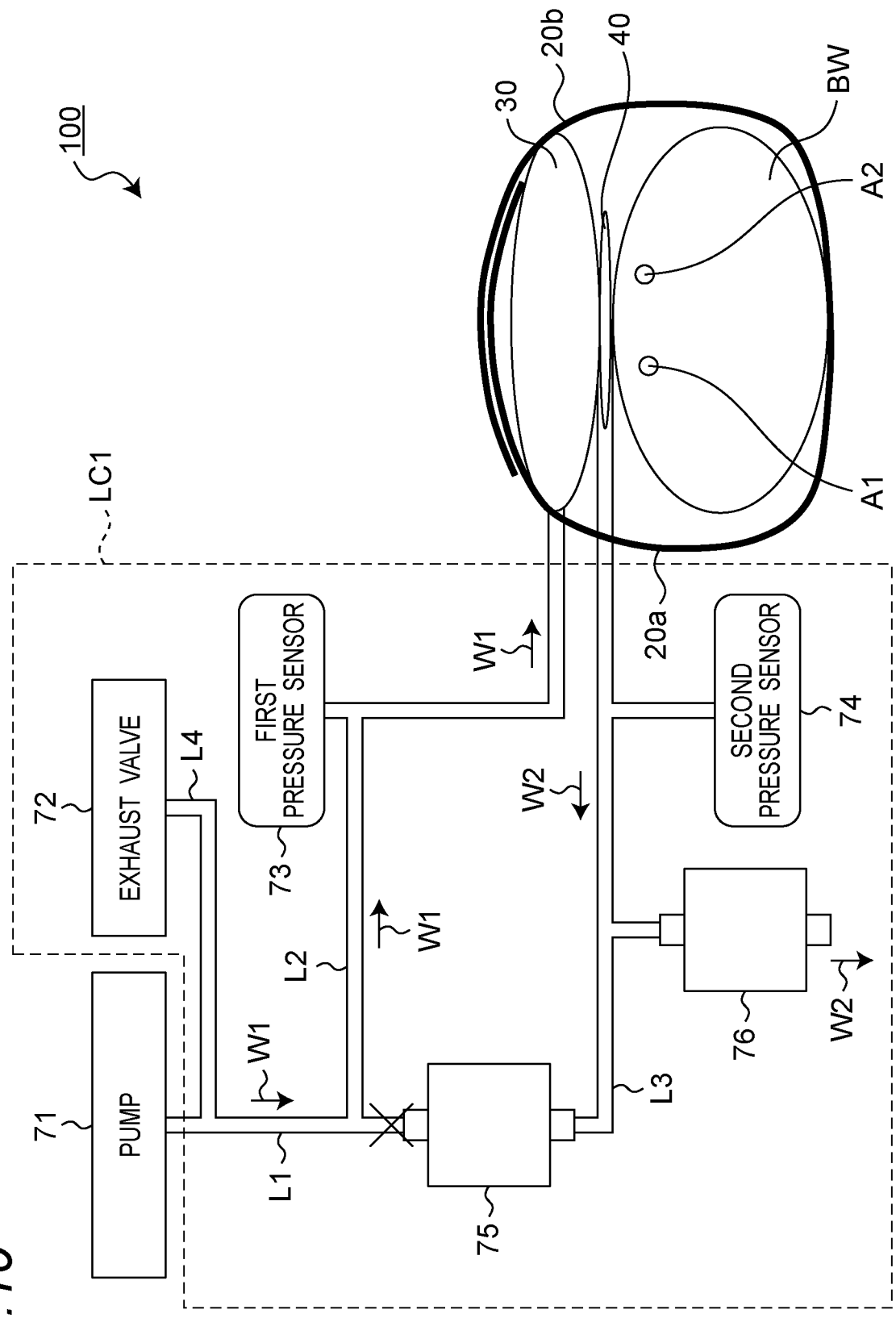
FIG. 10 is a diagram illustrating an operation of the blood pressure measurement preparation processing in the sphygmomanometer according to the first embodiment.
Figure 11:
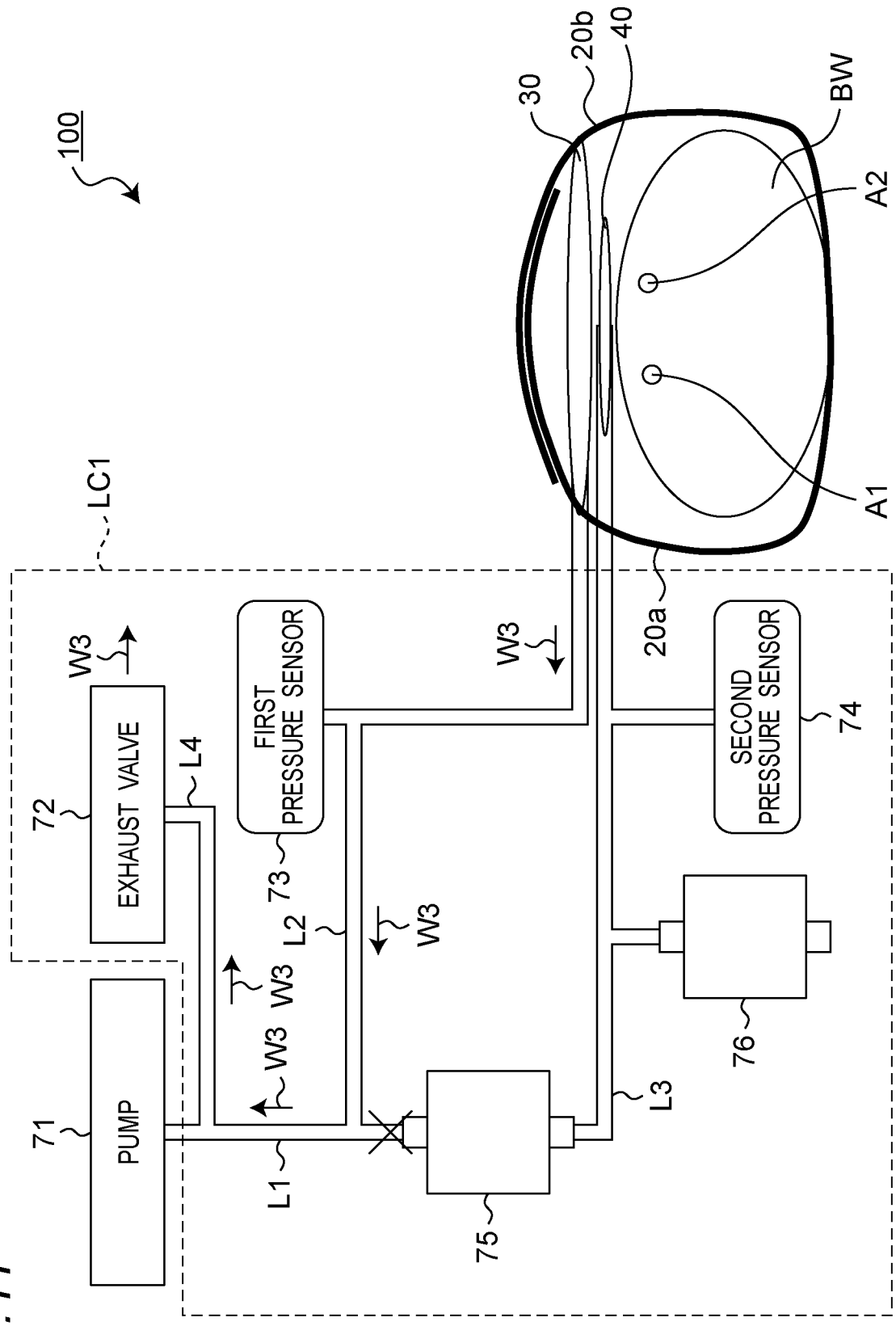
FIG. 11 is a diagram illustrating an operation of the blood pressure measurement preparation processing in the sphygmomanometer according to the first embodiment.

As can be seen from the above, by the control of the control unit 65, the fluid circuit LC1 according to the present embodiment supplies the pressurizing air from the pump 71 to the pressing cuff 30 when the pressing cuff 30 is operating, and causes the pressing cuff 30 to expand (FIG. 10). This enables the pressing cuff 30 to press the sensing cuff 40 toward the wrist BW. Further, by the control of the control unit 65, the fluid circuit LC1 discharges the pressurizing air from the pressing cuff 30 to the atmosphere when the pressing cuff 30 is not operating (FIG. 11).

(Operation of Blood Pressure Measurement Processing)

Figure 14:
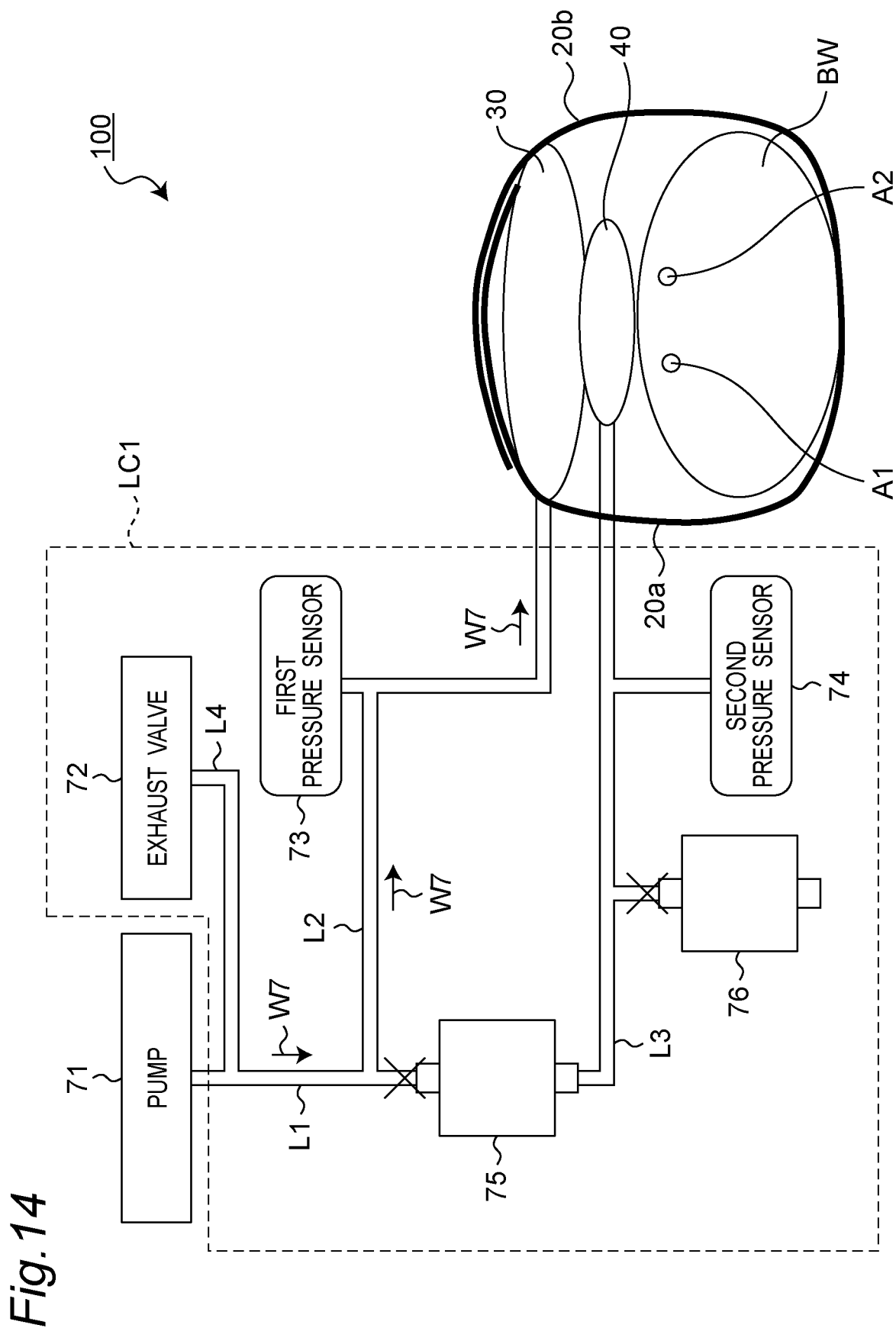
FIG. 14 is a diagram illustrating an operation of blood pressure measurement processing in the sphygmomanometer according to the first embodiment.

After step S1 of FIG. 7 (after the end of the flow of FIG. 8), the measurement processing unit 65D of the control unit 65 executes the blood pressure measurement processing (step S2 of FIG. 7). Specifically, the measurement processing unit 65D turns ON the pump 71 while maintaining the close state of the on-off valves 75 and 76 (the shut-off mode SM of the fluid circuit LC1). As shown by arrows W7 in FIG. 14, this enables the air to be sent into the pressing cuff 30 through the flow paths L1 and L2. Therefore, the pressing cuff 30 can be operated (expanded). The expanded pressing cuff 30 presses the sensing cuff 40 toward the wrist BW. The measurement processing unit 65D calculates the blood pressure of the wrist BW by the oscillometric method based on the pressure of the pressure transmitting air stored in the sensing cuff 40 while causing the sensing cuff 40 to compress the wrist BW. Details of the specific operation of the blood pressure measurement (blood pressure calculation) processing is described in, for example, JP 2018-102867 A.

Figure 15:
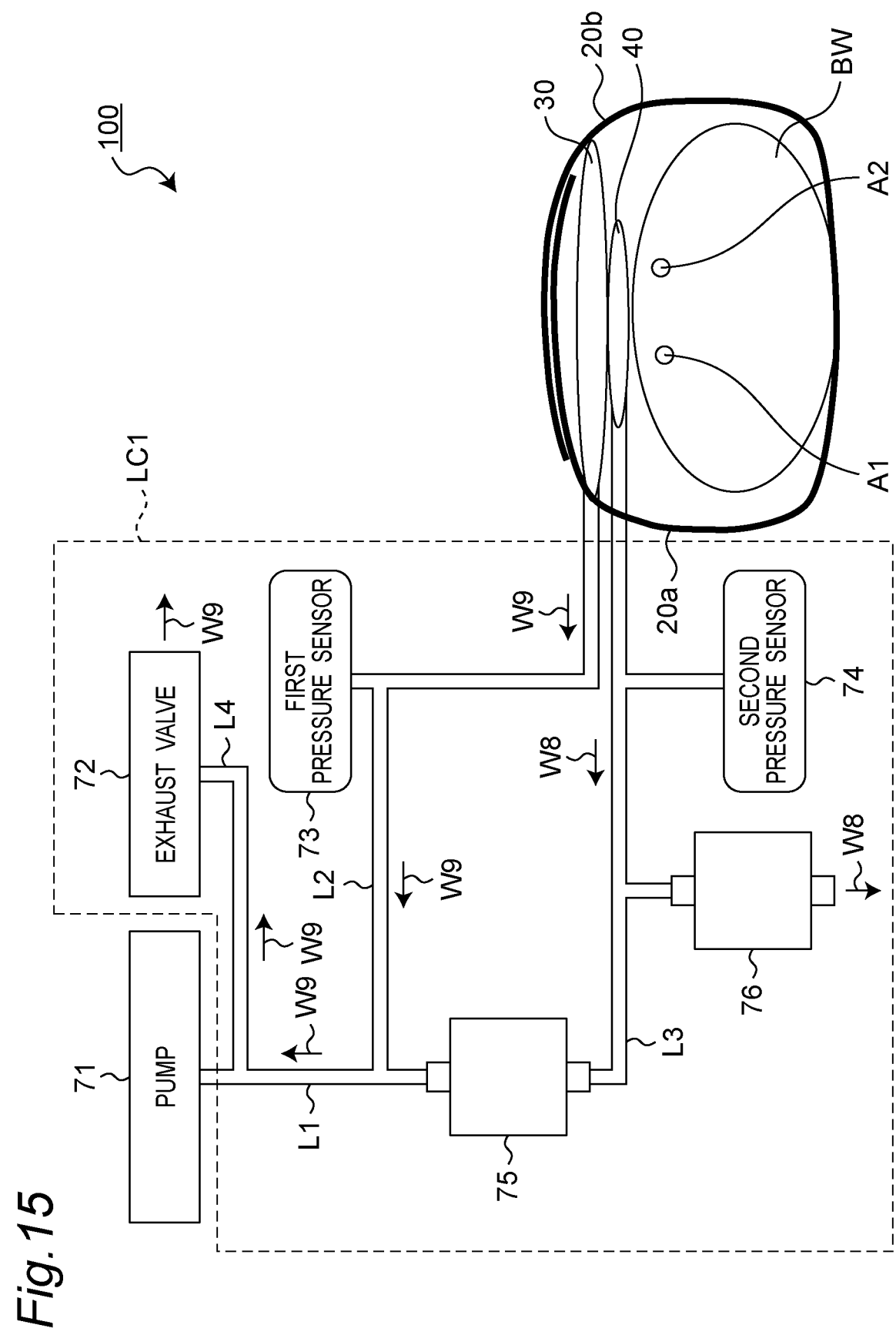
FIG. 15 is a diagram illustrating an operation of the blood pressure measurement processing in the sphygmomanometer according to the first embodiment.

After the calculation of blood pressure by the measurement processing unit 65D is completed, the measurement processing unit 65D turns the on-off valves 75 and 76 to the open state. This allows the air in the sensing cuff 40 to be discharged to the atmosphere through the flow path L3 and the on-off valve 76 as shown by arrows W8 in FIG. 15, and as shown in arrows W9 in FIG. 15, the air in the pressing cuff 30 is discharged to the atmosphere through the flow paths L2, L1, and L4 and the exhaust valve 72. Therefore, the pressure in the pressing cuff 30 and the pressure in the sensing cuff 40 become atmospheric pressure, and the blood pressure measurement processing ends.

Figure 16:
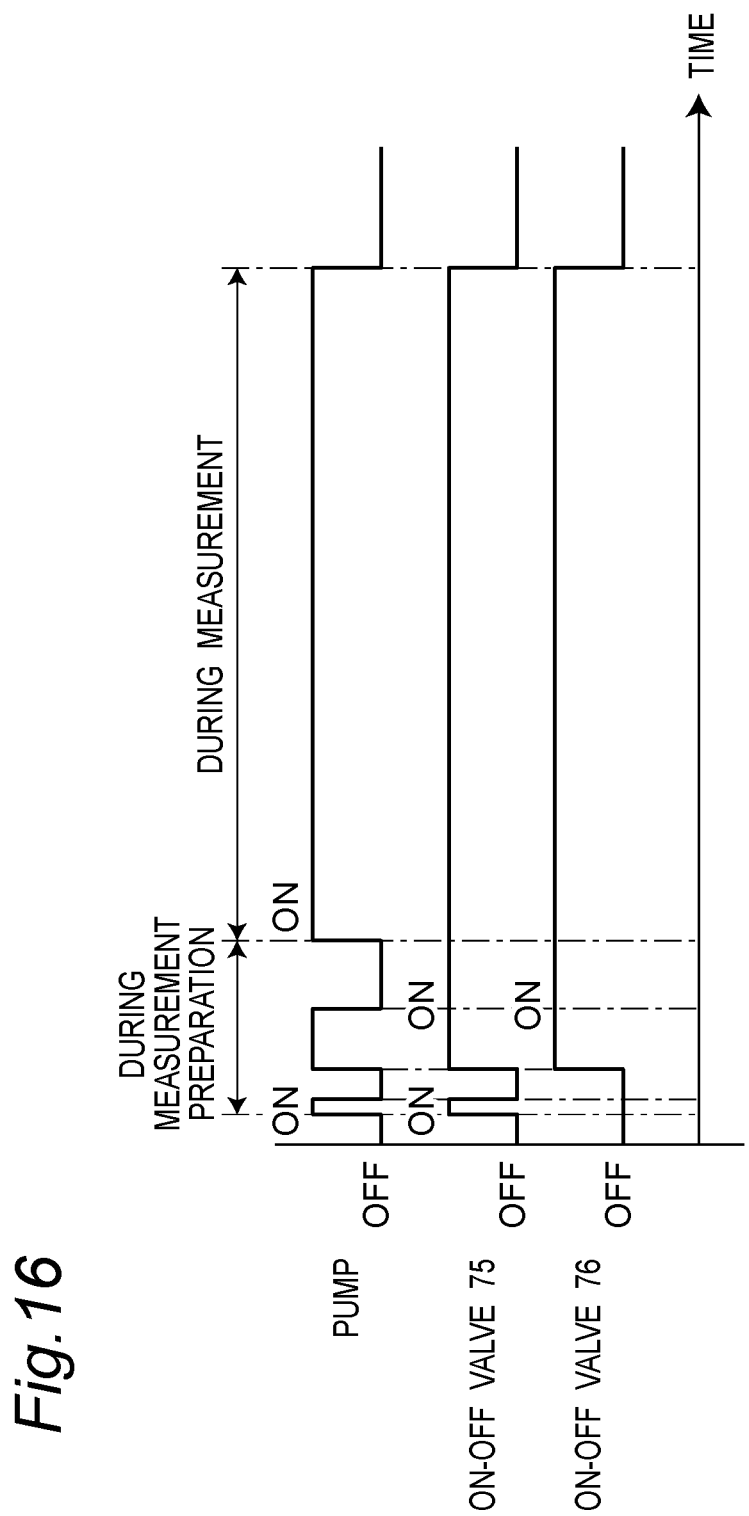
FIG. 16 is a diagram exemplifying, in chronological order, an operation timing of a pump and operation timings of on-off valves, at which a series of processing shown in FIGS. 8 to 15 can be executed.

FIG. 16 exemplifies, in chronological order, an operation timing of the pump 71 and operation timings of the on-off valves 75 and 76, at which the above series of processing can be executed. Note that ON of the pump 71 means the supply of air from the pump 71, and OFF of the pump 71 means the stop of the supply of air by the pump 71. Further, ON of the on-off valves 75 and 76 means the close state of the on-off valves 75 and 76, and OFF of the on-off valves 75 and 76 means the open state of the on-off valves 75 and 76.

Effects

In the sphygmomanometer 100 according to the present embodiment, the control unit 65 performs the predetermined control in the worn state of the belts 20a and 20b being worn around the wrist BW. That is, with the fluid circuit LC1 switched to the discharge mode DM, the first preparation processing unit 65A included in the control unit 65 operates the pressing cuff 30 to press the sensing cuff 40. This allows the air remaining in the sensing cuff 40 to be discharged to the atmosphere through the fluid circuit LC1. As a result, even if the air remains in the sensing cuff 40 after the blood pressure measurement using the sphygmomanometer 100 and before the next blood pressure measurement, the air is forcibly discharged from the sensing cuff 40.

Further, after the operation of the first preparation processing unit 65A, with the fluid circuit LC1 switched to the supply mode PM, the second preparation processing unit 65B causes the sensing cuff 40 to store the predetermined amount of pressure transmitting air received from the pump 71 through the fluid circuit LC1. As a result, the pressure transmitting air is stored in the sensing cuff 40. At this time, because the remaining air has been discharged from the sensing cuff 40 by the operation of the first preparation processing unit 65A, the amount of pressure transmitting air stored in the sensing cuff 40 becomes constant.

Further, after the operation of the second preparation processing unit 65B, with the fluid circuit LC1 switched to the shut-off mode SM, the measurement processing unit 65D operates the pressing cuff 30 to press the sensing cuff 40. Then, while causing the sensing cuff 40 to compress the wrist BW, the blood pressure of the wrist BW is calculated by the oscillometric method based on the pressure of the pressure transmitting air stored in the sensing cuff 40. Thereby, for example, as disclosed in JP 2018-102868 A and JP 2018-102867 A, as a result of setting the width dimensions of the belts 20a and 20b, the pressing cuff 30, and the sensing cuff 40 to be small (for example, about 25 mm), the blood pressure of the wrist BW is calculated accurately even when the compression loss of the pressing cuff 30 occurs during pressurization. In particular, as described above, because the amount of the pressure transmitting air stored in the sensing cuff 40 becomes constant after the operation of the second preparation processing unit 65B, the blood pressure can be calculated accurately.

Further, in the sphygmomanometer 100 according to the present embodiment, by the control of the control unit 65, the fluid circuit LC1 supplies the pressurizing air from the pump 71 to the pressing cuff 30 when the pressing cuff 30 is operating, and causes the pressing cuff 30 to expand and to press the sensing cuff 40 toward the wrist BW. On the other hand, by the control of the control unit 65, the fluid circuit LC1 discharges the pressurizing air from the pressing cuff 30 to the atmosphere when the pressing cuff 30 is not operating.

As described above, in the sphygmomanometer 100 according to the present embodiment, the pressing cuff 30 can be driven (expanded or contracted) by the pump 71, that is, by means common to the means for supplying the pressure transmitting air to the sensing cuff 40. Therefore, the configuration of the sphygmomanometer 100 can be simplified as compared with the case in which, for example, the pressing member is constituted of a mechanical actuator.

Further, in the sphygmomanometer 100 of the present embodiment, after the operation of the second preparation processing unit 65B and before the operation of the measurement processing unit 65D, with the fluid circuit LC1 switched to the shut-off mode SM, the third preparation processing unit 65C deactivates the pressing cuff 30 and causes the pressurizing air to be discharged to the atmosphere from the pressing cuff 30. As a result, the pressing applied to the sensing cuff 40 by the pressing cuff 30 is removed. Therefore, the pressure transmitting air stored in the sensing cuff 40 by the second preparation processing unit 65B can be distributed inside the sensing cuff 40. Therefore, when the blood pressure is measured by the measurement processing unit 65D, the sensing cuff 40 can correctly detect the pressure (pulse wave signal) generated by the arteries A1 and A2 in the wrist BW, making the accuracy of the blood pressure measurement improved.

Further, the sphygmomanometer 100 according to the present embodiment further includes the first pressure sensor (pressing cuff pressure sensor) 73 that measures the pressure in the pressing cuff 30. Therefore, the pressure in the pressing cuff 30 can be measured by the first pressure sensor 73. Therefore, the pressure in the pressing cuff 30 can be controlled by using the output of the first pressure sensor 73. This is particularly useful when the air remaining in the sensing cuff 40 is discharged to the atmosphere by the first preparation processing unit 65A and when the blood pressure is measured by the measurement processing unit 65D.

The sphygmomanometer 100 according to the present embodiment further includes the second pressure sensor (sensing cuff pressure sensor) 74 that measures the pressure in the sensing cuff 40. Therefore, the pressure in the sensing cuff 40 can be measured by using the second pressure sensor 74. Therefore, the pressure in the sensing cuff 40 can be controlled by using the output of the second pressure sensor 74. This is particularly useful when the second preparation processing unit 65B causes the sensing cuff 40 to store the predetermined amount of pressure transmitting air.

Further, in the sphygmomanometer 100 according to the present embodiment, the main body 10 is arranged at the portion opposite to the sensing cuff 40 in the circumferential direction of the belts 20a and 20b. Therefore, for example, when the sphygmomanometer 100 is worn around the wrist BW, the main body 10 is arranged on the back side surface of the wrist (the surface corresponding to the back side of the hand). As a result, the main body 10 is less likely to interfere with the daily life of the user.

Second Embodiment

Configuration of Sphygmomanometer According to Second Embodiment

Figure 17:
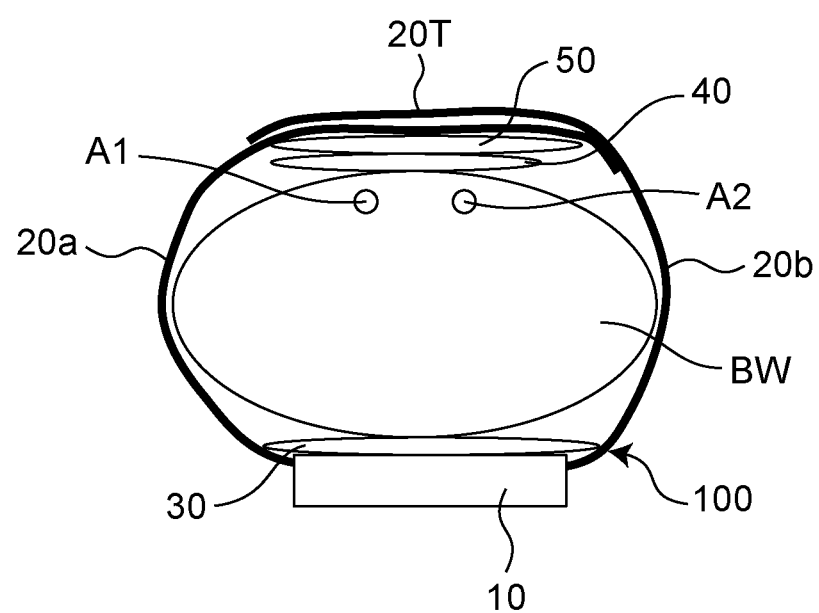
FIG. 17 is a cross-sectional view showing a state in which the sphygmomanometer according to the second embodiment is worn around the wrist.

FIG. 17 shows a schematic configuration of a sphygmomanometer 100 according to the present embodiment. As can be seen from the comparison between FIGS. 4 and 17, positions of the bag-shaped pressing cuffs 30 in the first embodiment and the second embodiment constituting the pressing members are different from each other. That is, in the present embodiment, the pressing cuff 30 is arranged at a portion of the inner circumferential side of the belts 20a and 20b that becomes opposite to the sensing cuff 40 in the worn state. In other words, in the present embodiment, the pressing cuff 30 is arranged on the side of the main body 10 and not on the side of the fastening part 20T of the belts 20a and 20b (see FIG. 17).

Further, in the present embodiment, as shown in FIG. 17, an auxiliary cuff 50 is added. In the configuration of FIG. 17, the auxiliary cuff 50 can be omitted. The auxiliary cuff 50 has a bag shape and is arranged between the belts 20a and 20b and the sensing cuff 40. In the worn state of the present embodiment, as shown in FIG. 17, the pressing cuff 30, the wrist BW, the sensing cuff 40, and the auxiliary cuff 50 are provided in this order from the main body 10 toward the fastening part 20T of the belts 20a and 20b. In the configuration example of FIG. 17, the main body 10 is arranged at a portion opposite to the sensing cuff 40 in the circumferential direction of the belts 20a and 20b.

The configuration other than the above is the same between the first embodiment and the second embodiment. Therefore, the description of the same configuration is omitted.

Figure 18:
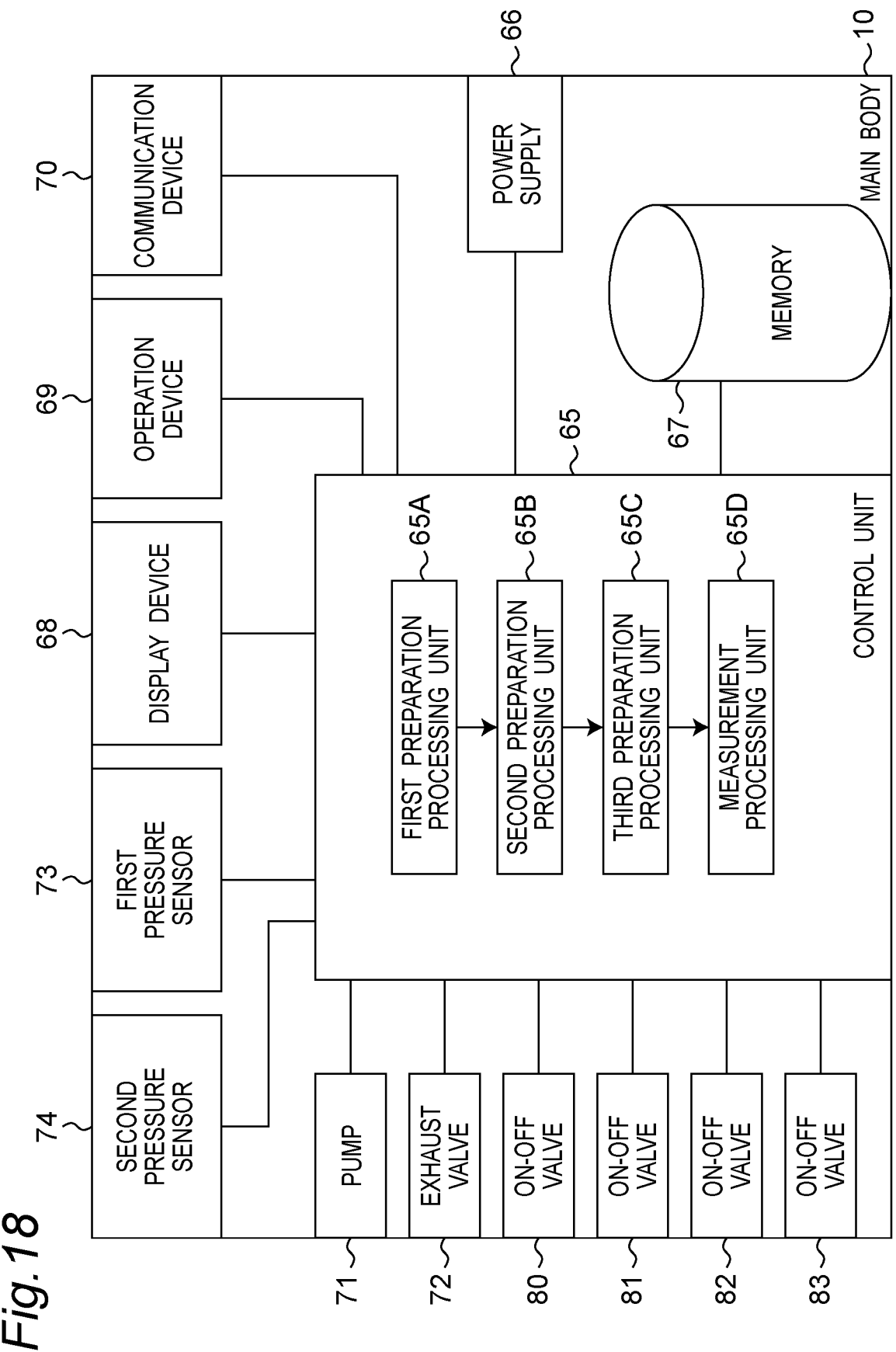
FIG. 18 is a diagram showing a schematic configuration of a control system of the sphygmomanometer according to the second embodiment.

FIG. 18 shows a schematic configuration of a control system of the sphygmomanometer 100 according to the present embodiment. As can be seen from the comparison between FIGS. 5 and 18, the sphygmomanometer 100 according to the first embodiment includes the two on-off valves 75 and 76, but the sphygmomanometer 100 according to the present embodiment has four on-off valves 80 to 83. Note that the control unit 65 controls the opening and closing of each of the on-off valves 80 to 83. Regarding the configuration of the control system, the configurations other than the above are the same between the first embodiment and the second embodiment. Therefore, the description of the same configuration is omitted.

Figure 19:
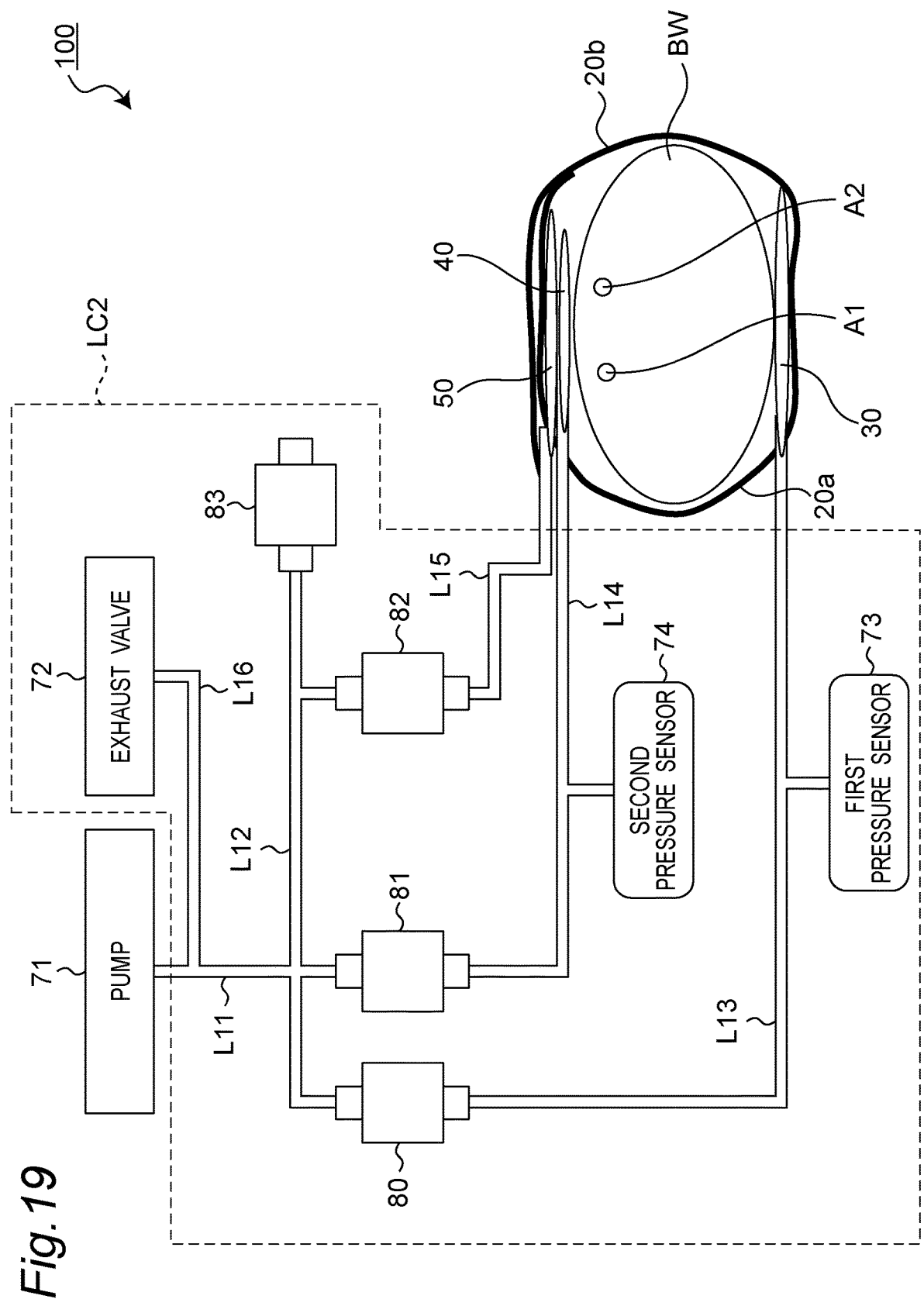
FIG. 19 is a diagram showing a schematic configuration of a flow path system of the sphygmomanometer according to the second embodiment.

FIG. 19 shows a schematic configuration of a flow path system of the sphygmomanometer 100 according to the present embodiment. The sphygmomanometer 100 shown in FIG. 19 includes the pump 71, a fluid circuit LC2, the pressing cuff 30, the sensing cuff 40, and the auxiliary cuff 50. Actually, the pump 71 and the fluid circuit LC2 are mounted on the main body 10 (see FIG. 17). However, in FIG. 19, the flow path system is developed in the same manner as shown in FIG. 6.

As in the first embodiment, the fluid circuit LC2 can be configured by switching between the supply mode PM, the discharge mode DM, and the shut-off mode SM. Further, the fluid circuit LC2 is configured to operate (expand) the pressing cuff 30 and the auxiliary cuff 50 forming the pressing member, or deactivate the same (exhaust air from the pressing cuff 30 and the auxiliary cuff 50).

Specifically, the fluid circuit LC2 according to the present embodiment includes the exhaust valve 72, each of the on-off valves 80 to 83, each of the pressure sensors 73 and 74, and each of flow paths L11 to L16. Here, air flows through each of the flow paths L11 to L16.

As shown in FIG. 19, the flow path L11 connects the pump 71 and the on-off valve 81. The flow path L12 connects the on-off valve 80 and the on-off valve 83 while merging with the flow path L11. The flow path L13 connects the on-off valve 80 and the pressing cuff 30. The flow path L14 connects the on-off valve 81 and the sensing cuff 40. The flow path L15 connects the on-off valve 82 and the auxiliary cuff 50. Further, the flow path L16 connects the exhaust valve 72 and the flow path L11. The on-off valve 80 is inserted between the flow path L12 and the flow path L13, the on-off valve 81 is inserted between the flow path L11 and the flow path L14, and the on-off valve 82 is inserted between the flow path L12 and the flow path L15. Further, the on-off valve 83 is inserted between the flow path L12 and the atmosphere.

The first pressure sensor (pressing cuff pressure sensor) 73 is connected to the flow path L13. Further, the second pressure sensor (sensing cuff pressure sensor) 74 is connected to the flow path L14.

Operation of Sphygmomanometer According to the Second Embodiment

After the sphygmomanometer 100 is worn around the wrist BW, the blood pressure measurement preparation processing (step S1) and the blood pressure measurement processing (step S2) shown in FIG. 7 are also performed on the sphygmomanometer 100 according to the present embodiment.

(Operation of Blood Pressure Measurement Preparation Processing)

Figure 20:
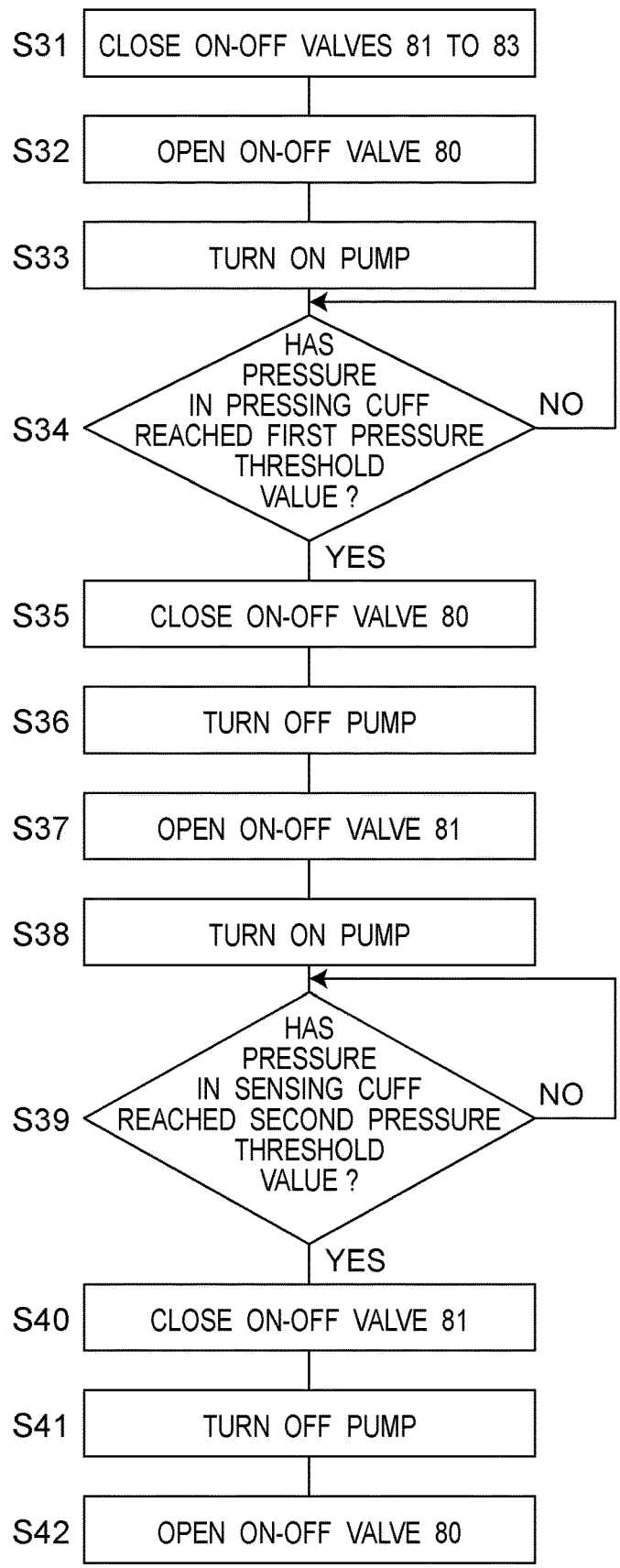
FIG. 20 is a flowchart showing an operation of blood pressure measurement preparation processing in the sphygmomanometer according to the second embodiment.

First, the details of the blood pressure measurement preparation processing (step S1) according to the present embodiment is described. FIG. 20 shows a specific flow of the blood pressure measurement preparation processing according to the present embodiment.

(1) In the state of the sphygmomanometer 100 being worn around the wrist BW, and with the fluid circuit LC2 switched to the discharge mode DM, the first preparation processing unit 65A of the control unit 65 operates (expands) the pressing cuff 30 to press the sensing cuff 40 to toward the wrist BW. Then, by the pressing, the air remaining in the sensing cuff 40 is discharged to the atmosphere through the fluid circuit LC2. More specific description is as follows.

Figure 21:
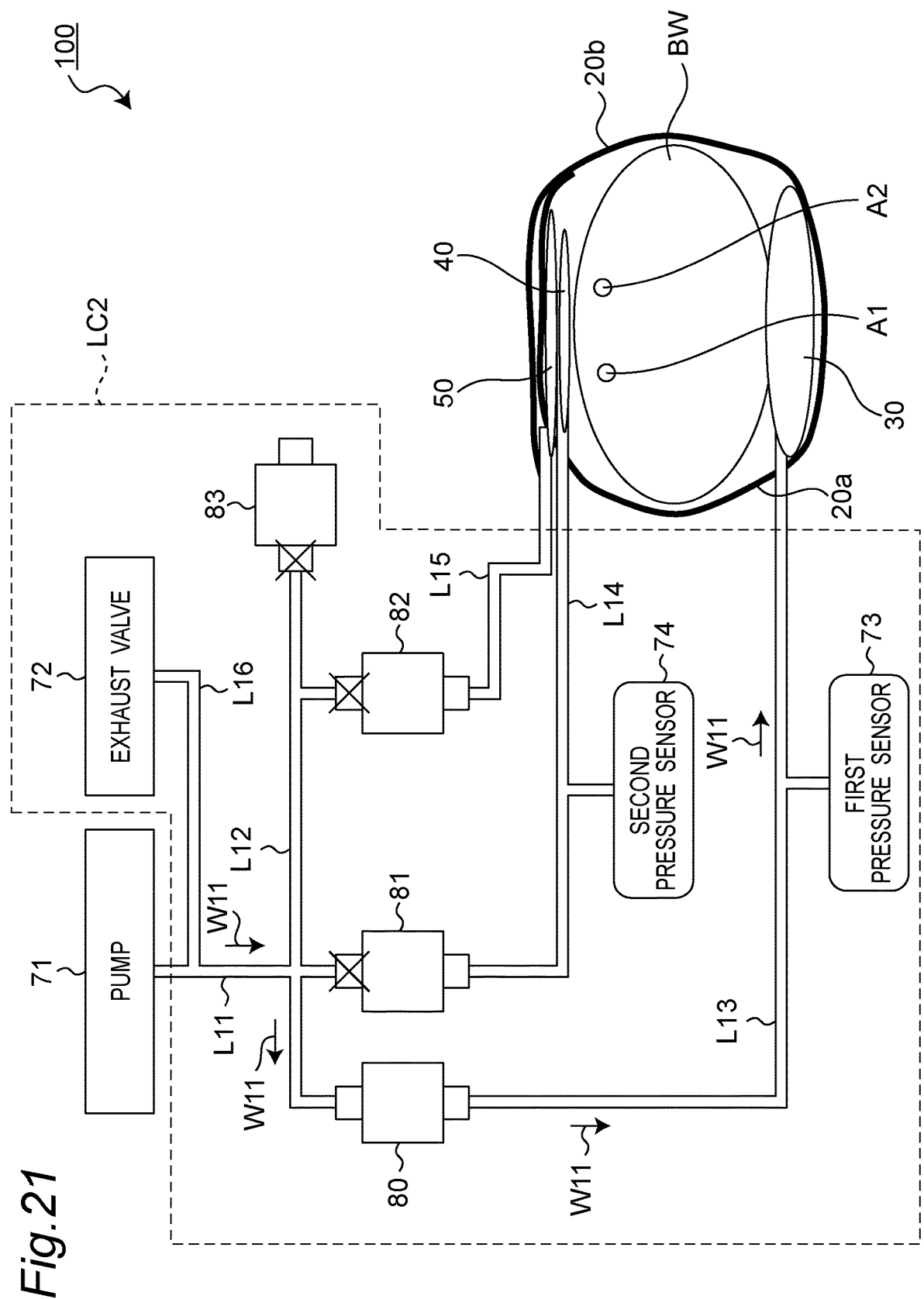
FIG. 21 is a diagram illustrating an operation of the blood pressure measurement preparation processing in the sphygmomanometer according to the second embodiment.

First, in step S31 of FIG. 20, the first preparation processing unit 65A closes the on-off valves 81 to 83 (see the "x" marks of the on-off valves 81 to 83 in FIG. 21). Further, in step S32, the first preparation processing unit 65A opens the on-off valve 80.

Next, in step S33, the first preparation processing unit 65A turns the pump 71 to the ON state. Thereby, as shown by arrows W11 in FIG. 21, the pump 71 can supply air to the pressing cuff 30 through the flow path L11, the on-off valve 80, and the flow path L13. By the supply of air in step S33, the pressing cuff 30 is filled with air, and the pressing cuff 30 expands (which can be grasped as the operation of the pressing cuff 30). Then, the expansion of the pressing cuff 30 generates a pressing force on the sensing cuff 40.

Next, in step S34, the first preparation processing unit 65A determines whether or not the measurement result (pressure in the pressing cuff 30) of the first pressure sensor 73 has reached the first pressure threshold value Pth1. As in the first embodiment, any value may be adopted as the first pressure threshold value Pth1, and as an example, a value of 30 mmHg may be adopted.

Figure 22:
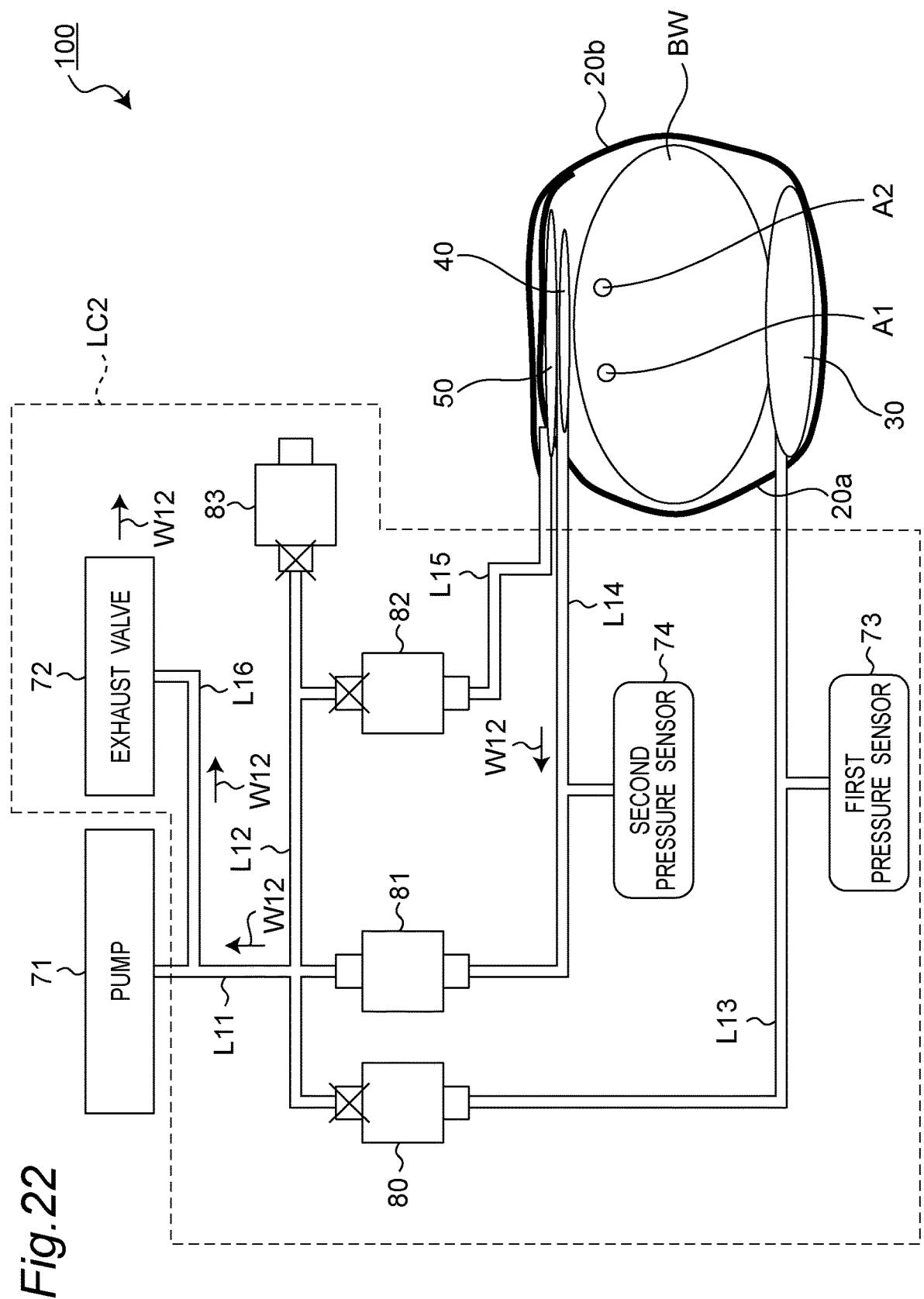
FIG. 22 is a diagram illustrating an operation of the blood pressure measurement preparation processing in the sphygmomanometer according to the second embodiment.

If the measurement result of the first pressure sensor 73 is less than the first pressure threshold value Pth1 (NO in step S34), the air supply from the pump 71 to the pressing cuff 30 is continued, while the determination processing in step S34 is also continued. On the other hand, if the measurement result of the first pressure sensor 73 has reached the first pressure threshold value Pth1 (YES in step S34), in step S35, the first preparation processing unit 65A closes the on-off valve 80 (see the "x" mark of the on-off valve 80 in FIG. 22).

Next, in step S36, the first preparation processing unit 65A turns the pump 71 to the OFF state. As a result, the supply of air from the pump 71 to the pressing cuff 30 is stopped. As described above, the opening and closing of the exhaust valve 72 is controlled in conjunction with the ON/OFF of the pump 71, and when the pump 71 is in the OFF state, the exhaust valve 72 is in the open state. Then, in step S37, the first preparation, processing unit 65A opens the on-off valve 81. With the stopping of the pump 71 (opening of the exhaust valve 72) and the opening the on-off valve 81, the first preparation processing unit 65A switches the fluid circuit LC2 to the discharge mode DM.

In the discharge mode DM of the fluid circuit LC2, as described above, the pressing cuff 30 operates (expands) to press the sensing cuff 40. Then, by the pressing, the air remaining in the sensing cuff 40 is discharged to the atmosphere through the flow path L14, the on-off valve 81, the flow paths L11 and L16, and the exhaust valve 72, as shown by arrows W12 in FIG. 22. In this way, the expansion of the pressing cuff 30 (the pressing force from the pressing cuff 30) is used to forcibly discharge an amount of air in the sensing cuff 40 from the sensing cuff 40 to the atmosphere, and thereby, an amount of remaining air in the sensing cuff 40 is brought close to zero.

(2) After the remaining air in the sensing cuff 40 is almost discharged to the atmosphere (after the operation of the first preparation processing unit 65A of the control unit 65), and with the fluid circuit LC2 switched to the supply mode PM, the second preparation processing unit 65B of the control unit 65 causes the sensing cuff 40 to store a predetermined amount (appropriate amount) of the pressure transmitting air received from the pump 71 through the fluid circuit LC2. More specific description is as follows.

Figure 23:
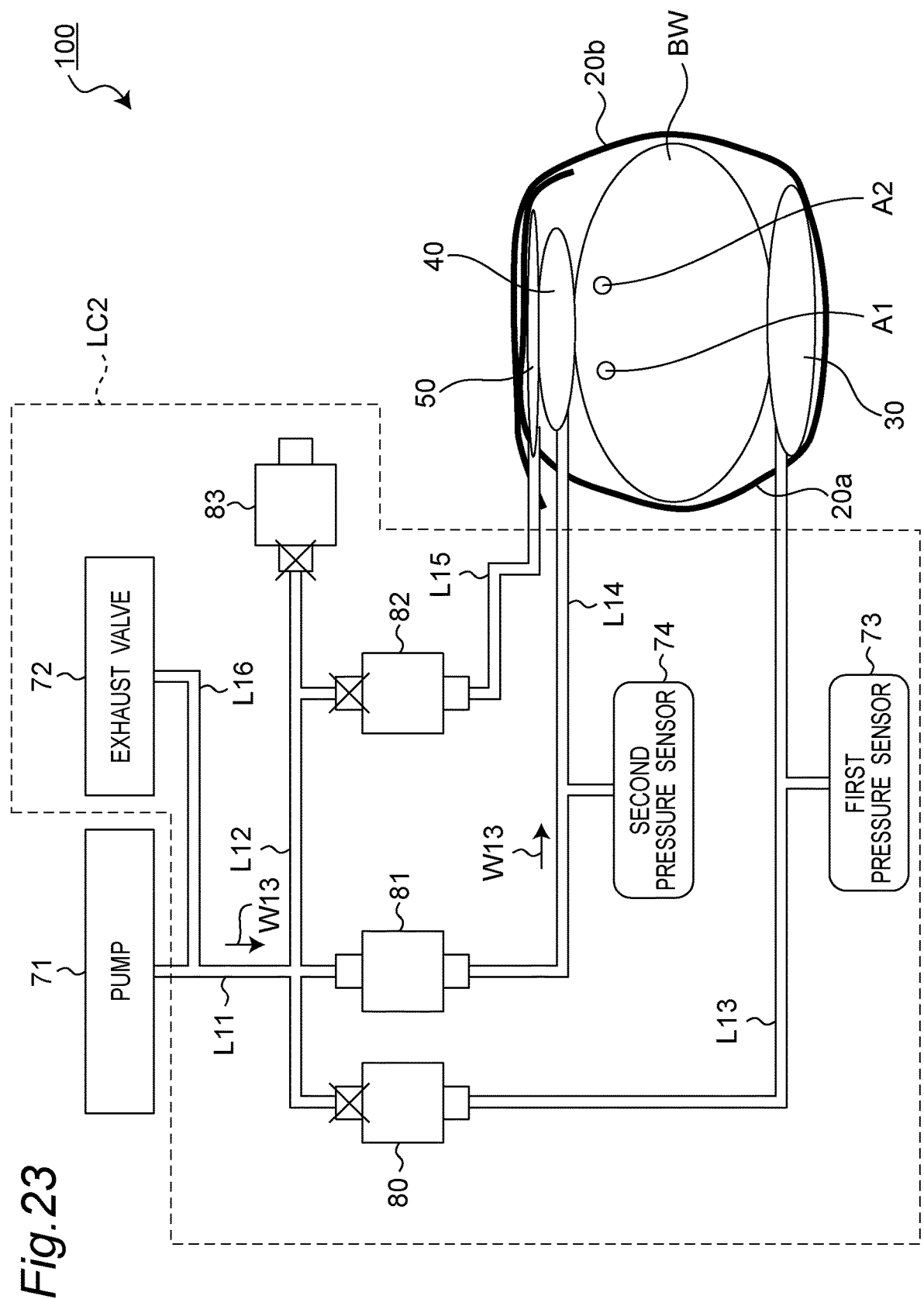
FIG. 23 is a diagram illustrating an operation of the blood pressure measurement preparation processing in the sphygmomanometer according to the second embodiment.

First, in step S38 of FIG. 20, the second preparation processing unit 65B turns ON the pump 71. When the pump 71 is turned ON and the on-off valve 81 is opened, the second preparation processing unit 65B switches the fluid circuit LC2 to the supply mode PM. In the supply mode PM, as shown by arrows W13 in FIG. 23, the pump 71 can supply air (which can be grasped as the appropriate amount of pressure transmitting fluid) to the sensing cuff 40 through the flow path L11, the on-off valve 81, and the flow path L14. By the supply of air in step S38, the sensing cuff 40 is caused to store an appropriate amount of pressure transmitting air (see FIG. 23). Note that an amount of the "appropriate amount" is described in, for example, JP 2018-102867 A which is already described.

Next, in step S39, the second preparation processing unit 65B determines whether or not the measurement result (pressure in the sensing cuff 40) of the second pressure sensor 74 has reached the second pressure threshold value Pth2. Note that any value can be adopted for the second pressure threshold value Pth2. For example, as the second pressure threshold value Pth2, less than 40 mmHg (preferably 30 mmHg) is adopted.

If the measurement result of the second pressure sensor 74 is less than the second pressure threshold value Pth2 (NO in step S39), the air supply from the pump 71 to the sensing cuff 40 is continued, while the determination processing in step S39 is also continued.

(3) On the other hand, if the measurement result of the second pressure sensor 74 has reached the second pressure threshold value Pth2 (YES in step S39), after the operation of the second preparation processing unit 65B, the third preparation processing unit 65C of the control unit 65 performs the following control before the blood pressure measurement.

Figure 24:
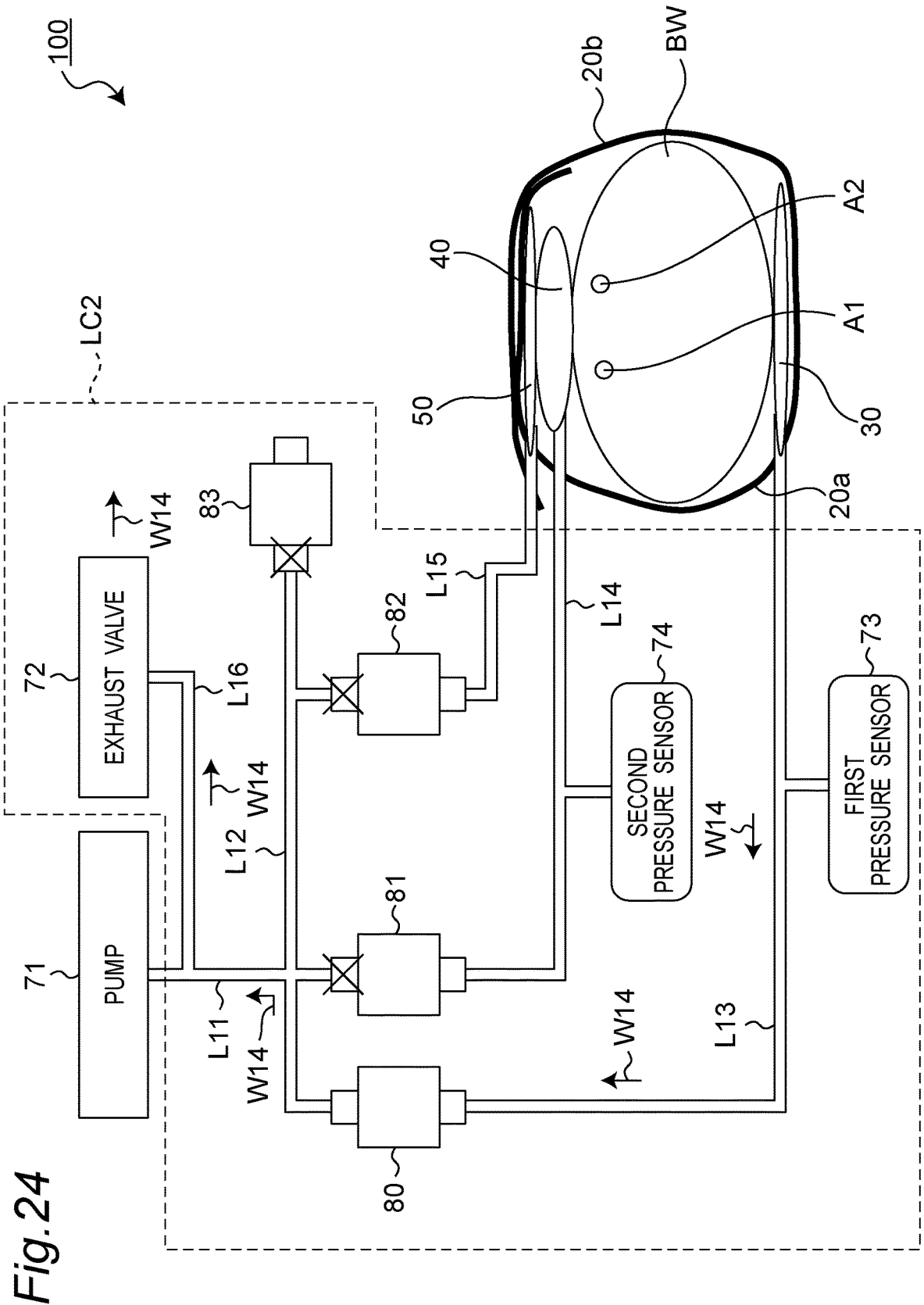
FIG. 24 is a diagram illustrating an operation of the blood pressure measurement preparation processing in the sphygmomanometer according to the second embodiment.

Specifically, in step S40 of FIG. 20, the third preparation processing unit 65C closes the on-off valve 81 (see the "x" mark of the on-off valve 81 in FIG. 24). With the closing of the on-off valve 81, the fluid circuit LC2 is switched to the shut-off mode SM.

Next, in step S41, the third preparation processing unit 65C turns the pump 71 to the OFF state. Next, in step S42, the third preparation processing unit 65C opens the on-off valve 80. As shown by arrows W14 in FIG. 24, this enables the air in the pressing cuff 30 which is not operating to be discharged to the atmosphere through the fluid circuit LC2 (the flow path L13, the on-off valve 80, the flow paths L12, L11, and L16, and the exhaust valve 72) which is in the shut-off mode SM. The above is the blood pressure measurement preparation processing (steps S1 in FIG. 7 and FIG. 20) by the preparation processing units 65A to 65C of the control unit 65.

As can be seen from the above, by the control of the control unit 65, the fluid circuit LC2 according to the present embodiment supplies the pressurizing air from the pump 71 to the pressing cuff 30 when the pressing cuff 30 is operating, and causes the pressing cuff 30 to expand (FIG. 21). This enables the pressing cuff 30 to press the sensing cuff 40 toward the wrist BW. In addition, by the control of the control unit 65, the fluid circuit LC2 discharges the pressurizing air from the pressing cuff 30 to the atmosphere when the pressing cuff 30 is not operating (FIG. 24).

(Operation of Blood Pressure Measurement Processing)

Figure 25:
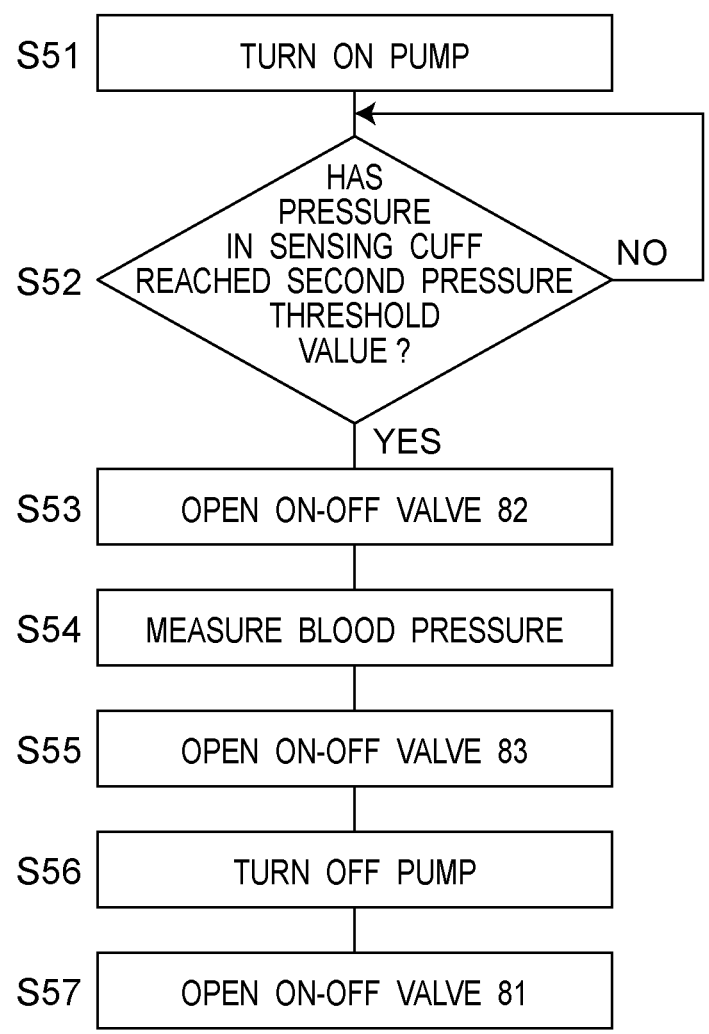
FIG. 25 is a flowchart showing an operation of blood pressure measurement processing in the sphygmomanometer according to the second embodiment.

After step S1 of FIG. 7 (after the end of the flow of FIG. 20), the measurement processing unit 65D of the control unit 65 executes the blood pressure measurement processing (step S2 of FIG. 7). FIG. 25 shows a specific flow of the blood pressure measurement processing according to the present embodiment.

Figure 26:
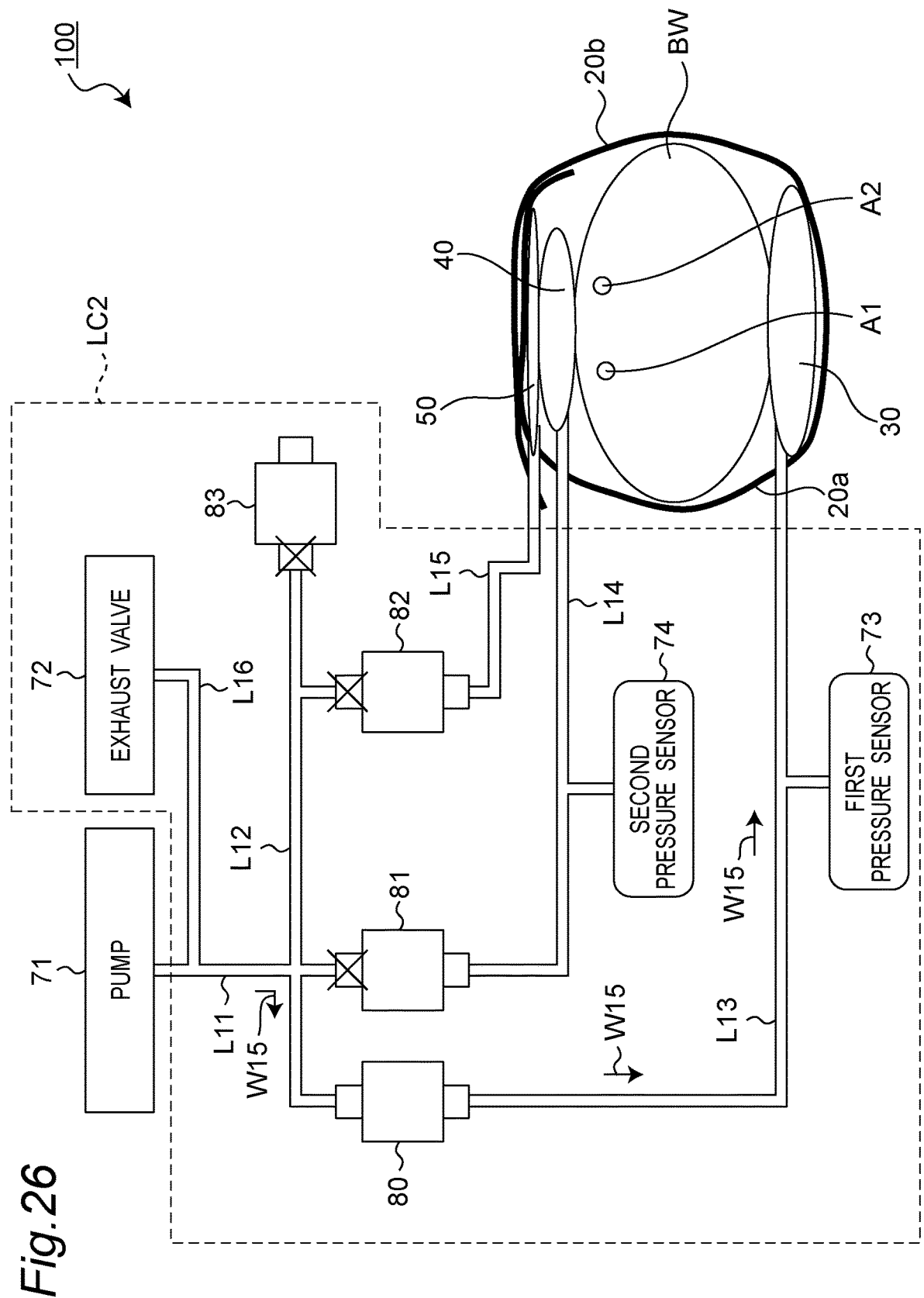
FIG. 26 is a diagram illustrating an operation of the blood pressure measurement processing in the sphygmomanometer according to the second embodiment.

Specifically, in step S51 of FIG. 25, the measurement processing unit 65D turns ON the pump 71 while maintaining the close state of the on-off valves 81 to 83 (the shut-off mode SM of the fluid circuit LC2). As shown by arrows W15 in FIG. 26, this enables the air to be sent into the pressing cuff 30 through the flow path L11, the on-off valve 80, and the flow path L13. Therefore, the pressing cuff 30 can be operated (expanded). The expanded pressing cuff 30 presses the sensing cuff 40 toward the wrist BW through the belts 20a and 20b.

Next, in step S52, the measurement processing unit 65D determines whether or not the measurement result (pressure in the sensing cuff 40) of the second pressure sensor 74 has reached the second pressure threshold value Pth2. If the measurement result of the second pressure sensor 74 is less than the second pressure threshold value Pth2 (NO in step S52), the air supply from the pump 71 to the pressing cuff 30 is continued, while the determination processing in step S52 is also continued. On the other hand, if the measurement result of the second pressure sensor 74 has reached the second pressure threshold value Pth2 (YES in step S52), the measurement processing unit 65D opens the on-off valve 82 (step S53).

Figure 27:
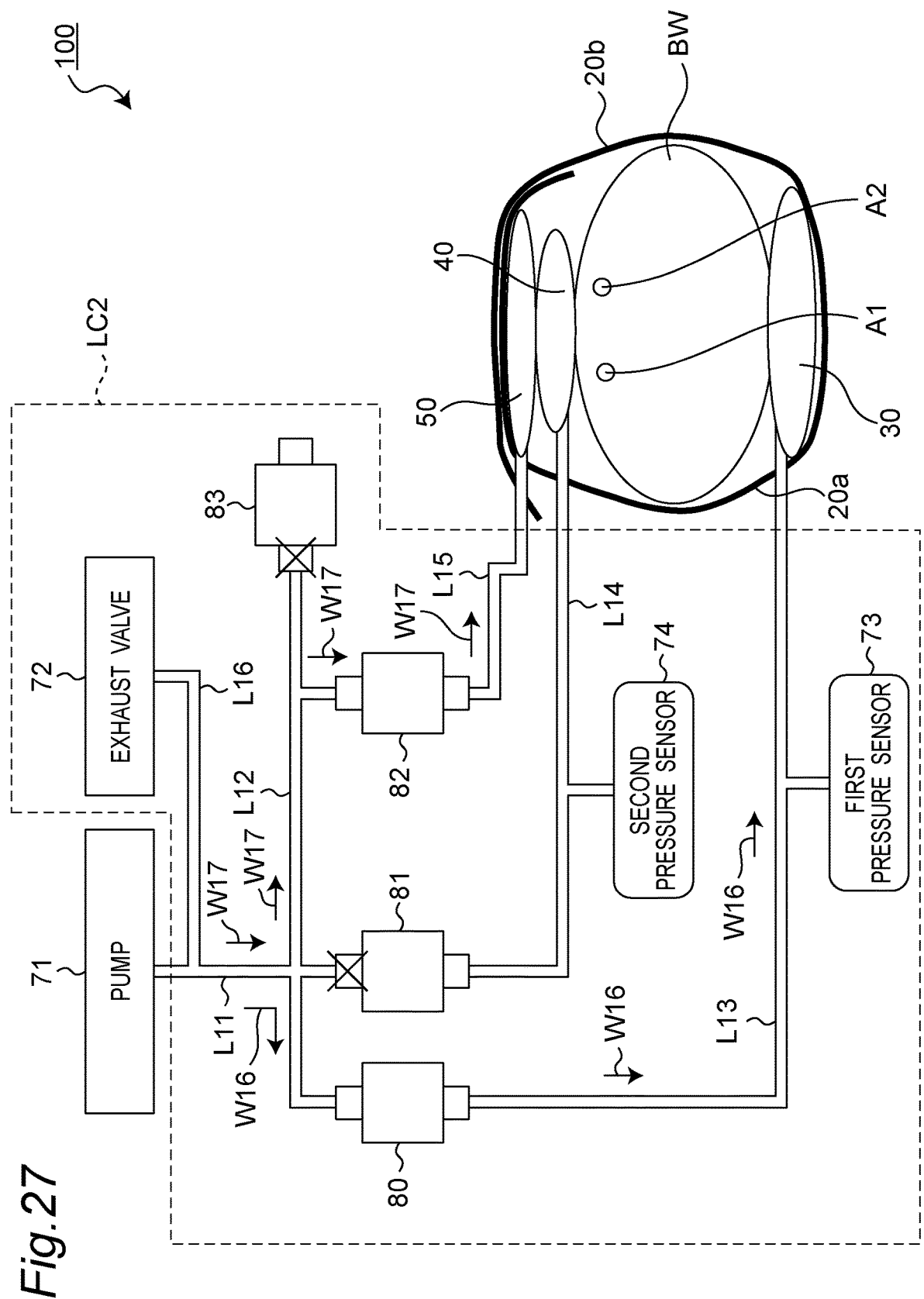
FIG. 27 is a diagram illustrating an operation of the blood pressure measurement processing in the sphygmomanometer according to the second embodiment.

Thereby, as shown by arrows W16 in FIG. 27, the air is supplied from the pump 71 into the pressing cuff 30 through the flow paths L11 and L12, the on-off valve 80, and the flow path L13. Further, as shown by arrows W17 in FIG. 27, the air is supplied from the pump 71 into the auxiliary cuff 50 through the flow path L11, the on-off valve 82, and the flow path L15. In this way, while pressurizing the pressing cuff 30 and the auxiliary cuff 50 gradually (that is, while causing the sensing cuff 40 to compress the wrist BW), based on the pressure of the pressure transmitting air stored in the sensing cuff 40, the blood pressure of the wrist BW is calculated by the oscillometric method (step S54).

Figure 28:
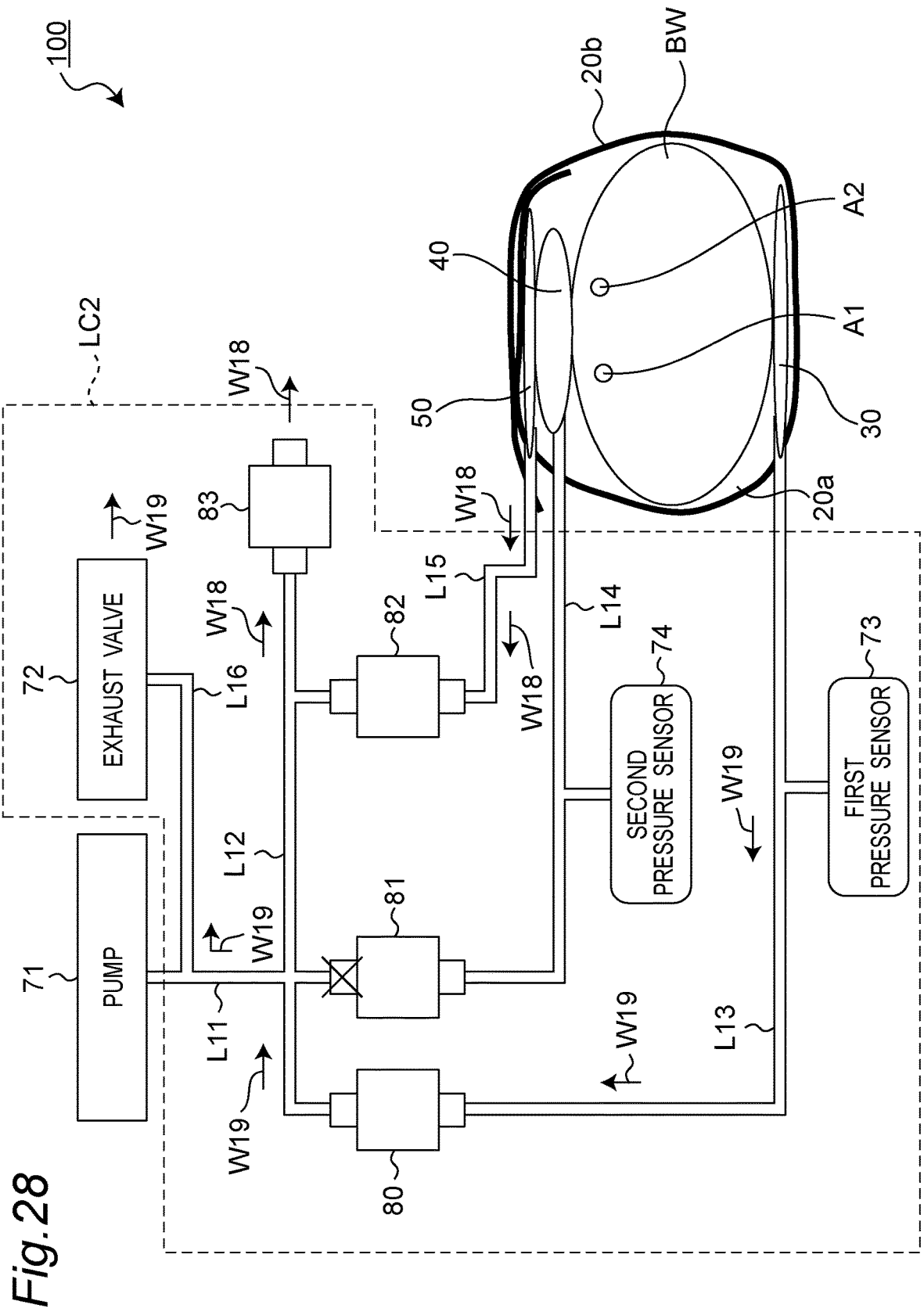
FIG. 28 is a diagram illustrating an operation of the blood pressure measurement processing in the sphygmomanometer according to the second embodiment.

After the calculation of blood pressure by the measurement processing unit 65D is completed, in step S55, the measurement processing unit 65D turns the on-off valve 83 to the open state. Next, in step S56, the measurement processing unit 85D turns OFF the pump 71. Thereby, for example, the air in the auxiliary cuff 50 is discharged to the atmosphere through the flow path L15, the on-off valve 82, the flow path L12, and the on-off valve 83, as shown by arrows W18 in FIG. 28, and the air in the pressing cuff 30 is discharged to the atmosphere through the flow path L13, the on-off valve 80, the flow path L12, L11, and L16, and the exhaust valve 72, as shown by arrows W19 in FIG. 28. Therefore, the pressure in the pressing cuff 30 and the pressure in the auxiliary cuff 50 become atmospheric pressure.

Figure 29:
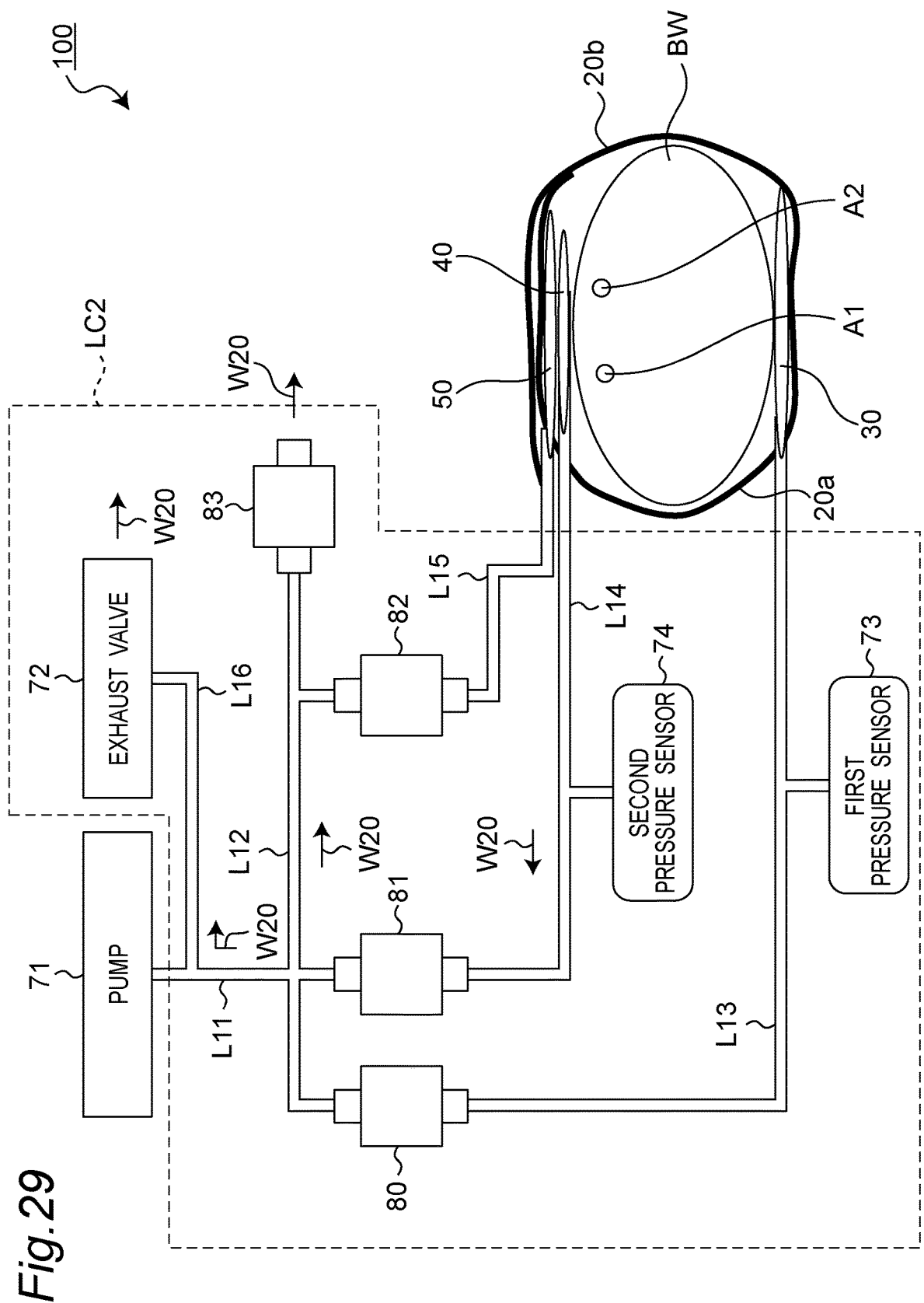
FIG. 29 is a diagram illustrating an operation of the blood pressure measurement processing in the sphygmomanometer according to the second embodiment.

Next, in step S57, the measurement processing unit 65D turns the on-off valve 81 to the open state. Thereby, for example, as indicated by arrows W20 in FIG. 29, the air in the sensing cuff 40 is discharged to the atmosphere through the flow path L14, the on-off valve 81, the flow paths L11 and L16, and the exhaust valve 72, and/or, through the flow path L14, the on-off valve 81, the flow path L12, and the on-off valve 83. Therefore, the pressure in the sensing cuff 40 becomes atmospheric pressure, and the blood pressure measurement processing ends.

Effects

The sphygmomanometer 100 according to the present embodiment has the following effects in addition to the effects described in the first embodiment. That is, in the sphygmomanometer 100 according to the present embodiment, the pressing cuff 30 is arranged at the portion of the inner circumferential side of the belts 20a and 20b that becomes opposite to the sensing cuff 40 in the worn state. Then, by the control of the control unit 65, the fluid circuit LC2 supplies the pressurizing fluid from the pump 71 to the pressing cuff 30 when the pressing cuff 30 is operating, and causes the pressing cuff 30 to expand. The expansion of the pressing cuff 30 causes the sensing cuff 40 to be pressed toward the wrist BW. On the other hand, by the control of the control unit 65, the fluid circuit LC2 discharges the pressurizing air from the pressing cuff 30 to the atmosphere when the pressing cuff 30 is not operating.

Thereby, the pressing cuff 30 can be driven (expanded or contracted) by the pump 71, that is, by means common to the means for supplying the pressure transmitting air to the sensing cuff 40. Therefore, the configuration of the sphygmomanometer 100 can be simplified as compared with the case in which, for example, the pressing member is constituted of a mechanical actuator. Further, the pressing cuff 30 is arranged at the portion of the inner circumferential side of the belts 20a and 20b that becomes opposite to the sensing cuff 40 in the worn state. For example, the pressing cuff 30 is arranged on the back side surface of the wrist (the surface corresponding to the back side of the hand) in the worn state, and is expanded to increase the tension of the belts 20a and 20b. As a result, the portion of the belts 20a and 20b facing the sensing cuff 40 requires only a small amount of stroke to press the sensing cuff 40 toward the wrist BW. Therefore, an escaping distance of the arteries A1 and A2 (positioned in the wrist BW) pushed by the sensing cuff 40 is reduced (see, for example, JP 2017-006488 A). Therefore, the blood pressure can be calculated more accurately.

Further, also in the sphygmomanometer 100 according to the present embodiment, the main body 10 is arranged at the portion opposite to the sensing cuff 40 in the circumferential direction of the belts 20a and 20b, as in the first embodiment. As described above, the pressing cuff 30 is arranged at the portion of the inner peripheral side of the belts 20a and 20b that becomes opposite to the sensing cuff 40. Therefore, a distance from the pump 71 mounted on the main body 10 to the pressing cuff 30 can be shortened as much as possible, and the sphygmomanometer 100 can be made compact.

In each of the above embodiments, the control unit 65 includes the CPU, but the present invention is not limited to this. The control unit 65 may include a logic circuit (integrated circuit) such as a programmable logic device (PLD) or a field programmable gate array (FPGA).

As described above, a sphygmomanometer according to the present disclosure is a sphygmomanometer comprising:
 a main body mounted with a pump;
 a belt extending from the main body and worn around a measurement target site;
 a sensing cuff arranged, in a worn state of the belt being worn around the measurement target site, at a portion of an inner circumferential side of the belt that crosses an artery passing portion of the measurement target site, and configured in a bag shape so as to allow storage of a pressure transmitting fluid;
 a pressing member that presses the sensing cuff toward the measurement target site and causes the sensing cuff to compress the measurement target site;
 a fluid circuit that can be configured by switching among a supply mode of suppling the pressure transmitting fluid from the pump to the sensing cuff, a discharge mode of discharging the fluid from the sensing cuff to atmosphere, and a shut-off mode of shutting off fluid supply to the sensing cuff and fluid discharge from the sensing cuff; and
 a control unit, wherein,
 the control unit includes, in the worn state:
 a first preparation processing unit that, with the fluid circuit switched to the discharge mode, operates the pressing member to press the sensing cuff toward the measurement target site and discharges a fluid remaining in the sensing cuff to the atmosphere through the fluid circuit;
 a second preparation processing unit that, with the fluid circuit switched to the supply mode after operation of the first preparation processing unit, causes the sensing cuff to store a predetermined amount of the pressure transmitting fluid received from the pump through the fluid circuit; and a measurement processing unit that, with the fluid circuit switched to the shut-off mode after operation of the second preparation processing unit, operates the pressing member to press the sensing cuff toward the measurement target site and causes the sensing cuff to compress the measurement target site, and meanwhile, calculates a blood pressure of the measurement target site based on a pressure of the pressure transmitting fluid stored in the sensing cuff by an oscillometric method.

The "fluid" is typically air, but may be other gas or liquid.

The "inner circumferential side" of the belt refers to a side facing the measurement target site in the worn state wrapped around the measurement target site.

In the sphygmomanometer of the present disclosure, the control unit performs predetermined control in the worn state of the belt being worn around the measurement target site. That is, with the fluid circuit switched to the discharge mode, the first preparation processing unit included in the control unit operates the pressing member to press the sensing cuff and causes the fluid remaining in the sensing cuff to be discharged to the atmosphere through the fluid circuit. As a result, even if the fluid remains in the sensing cuff after the blood pressure measurement by the sphygmomanometer and before the next blood pressure measurement, the fluid is discharged from the sensing cuff. Next, after the operation of the first preparation processing unit, with the fluid circuit switched to the supply mode, the second preparation processing unit causes the sensing cuff to store the predetermined amount of the pressure transmitting fluid received from the pump through the fluid circuit. As a result, the pressure transmitting fluid is stored in the sensing cuff. At this time, because the remaining fluid has been discharged from the sensing cuff by the operation of the first preparation processing unit, the amount of the pressure transmitting fluid stored in the sensing cuff becomes constant. Next, after the operation of the second preparation processing unit, with the fluid circuit switched to the shut-off mode, the measurement processing unit operates the pressing member to press the sensing cuff toward the measurement target site and causes the sensing cuff to compress the measurement target site, and meanwhile, calculates the blood pressure of the measurement target site based on a pressure of the pressure transmitting fluid stored in the sensing cuff by the oscillometric method. Thereby, for example, as disclosed in JP 2018-102868 A and JP 2018-102867 A, as a result of setting width dimensions of the belt, the pressing member, and the sensing cuff (as appropriate, these are collectively referred to as a "cuff") to be small (for example, about 25 mm), the blood pressure of the measurement target site is calculated accurately even when the compression loss of the pressing member occurs during pressurization. In particular, as described above, because the amount of the pressure transmitting fluid stored in the sensing cuff becomes constant after the operation of the second preparation processing unit, the blood pressure is calculated accurately.

In the sphygmomanometer of one embodiment,
the pressing member includes a pressing cuff having a bag shape and arranged between the belt and the sensing cuff, and
under control of the control unit, when the pressing member is operating, the fluid circuit supplies a pressurizing fluid from the pump to the pressing cuff to expand the pressing cuff and causes the sensing cuff to press toward the measurement target site, and meanwhile, when the pressing member is not operating, the fluid circuit discharges the pressurizing fluid to the atmosphere from the pressing cuff.

In the sphygmomanometer of this one embodiment, the pressing cuff can be driven (expanded or contracted) by the pump, that is, by means common to the means for supplying the pressure transmitting fluid to the sensing cuff. Therefore, the configuration of the sphygmomanometer can be simplified as compared with the case in which, for example, the pressing member is constituted of such as a mechanical actuator.

In the sphygmomanometer of one embodiment,
the pressing member includes a pressing cuff having a bag shape and arranged at a portion of the inner circumferential side of the belt that becomes opposite to the sensing cuff in the worn state, and
under control of the control unit, when the pressing member is operating, the fluid circuit supplies a pressurizing fluid from the pump to the pressing cuff to expand the pressing cuff and causes the sensing cuff to press toward the measurement target site, and meanwhile, when the pressing member is not operating, the fluid circuit discharges the pressurizing fluid to the atmosphere from the pressing cuff.

In the sphygmomanometer of this one embodiment, the pressing cuff can be driven (expanded or contracted) by the pump, that is, by means common to the means for supplying the pressure transmitting fluid to the sensing cuff. Therefore, the configuration of the sphygmomanometer is simplified as compared with the case in which, for example, the pressing member is constituted of such as a mechanical actuator. Further, the pressing cuff is arranged at the portion of the inner circumferential side of the belt that becomes opposite to the sensing cuff in the worn state. For example, if the measurement target site is a wrist, the pressing cuff is arranged on a back side surface of the wrist (the surface corresponding to the back side of the hand) in the worn state, and is expanded to increase the tension of the belt. As a result, the portion of the belt facing the sensing cuff requires only a small amount of stroke to press the sensing cuff toward the measurement target site. Therefore, an escaping distance of the artery (positioned in the measurement target site) pushed by the sensing cuff is reduced (see, for example, JP 2017-006488 A). Therefore, the blood pressure is calculated more accurately.

In the sphygmomanometer of one embodiment,
the control unit includes a third preparation processing unit that operates after the operation of the second preparation processing unit and before operation of the measurement processing unit, and
with the fluid circuit switched to the shut-off mode, the third preparation processing unit deactivates the pressing member and discharges the pressurizing fluid from the pressing cuff to the atmosphere.

In the sphygmomanometer of this one embodiment, after the operation of the second preparation processing unit and before the operation of the measurement processing unit, with the fluid circuit switched to the shut-off mode, the third preparation processing unit deactivates the pressing member, and causes the pressurizing fluid to be discharged to the atmosphere from the pressing cuff. As a result, the pressing applied to the sensing cuff by the pressing cuff is removed. Therefore, the pressure transmitting fluid stored in the sensing cuff by the second preparation processing unit can be distributed inside the sensing cuff. Therefore, when the blood pressure is measured by the measurement processing unit, the sensing cuff can correctly detect the pressure (pulse wave signal) generated by the artery at the measurement target site, making the accuracy of the blood pressure measurement improved.

The sphygmomanometer of one embodiment further comprises a pressing cuff pressure sensor configured to measure pressure in the pressing cuff.

In the sphygmomanometer of this one embodiment, the pressure in the pressing cuff can be measured by the pressing cuff pressure sensor. Therefore, the pressure in the pressing cuff can be controlled by using the output of the pressing cuff pressure sensor. This is particularly useful when the fluid remaining in the sensing cuff is discharged to the atmosphere by the first preparation processing unit and when the blood pressure is measured by the measurement processing unit.

The sphygmomanometer of one embodiment further comprises a sensing cuff pressure sensor configured to measure pressure in the sensing cuff.

In the sphygmomanometer of this one embodiment, the pressure in the sensing cuff can be measured by the sensing cuff pressure sensor. Therefore, the pressure in the sensing cuff can be controlled by using the output of the sensing cuff pressure sensor. This is particularly useful when the predetermined amount of pressure transmitting fluid is stored in the sensing cuff by the second preparation processing unit.

In the sphygmomanometer of one embodiment, the main body is arranged at a portion opposite to the sensing cuff in a circumferential direction of the belt.

In the sphygmomanometer of one embodiment, the main body is arranged at the portion opposite to the sensing cuff in the circumferential direction of the belt. Therefore, for example, when this sphygmomanometer constitutes a wrist-type sphygmomanometer, the main body is arranged on the back side surface of the wrist (the surface corresponding to the back side of the hand) in the worn state. As a result, the main body is less likely to interfere with the daily life of a user. Further, when the pressing cuff is arranged at the portion of the inner circumferential side of the belt that becomes opposite to the sensing cuff, a distance from the pump to the pressing cuff can be shortened as much as possible, and the sphygmomanometer can also be made compact.

In another aspect, a blood pressure measurement method according to the present disclosure is a blood pressure measurement method that uses a sphygmomanometer comprising: a main body mounted with a pump; a belt extending from the main body and worn around a measurement target site; a sensing cuff arranged, in a worn state of the belt being worn around the measurement target site, at a portion of an inner circumferential side of the belt that crosses an artery passing portion of the measurement target site, and configured in a bag shape so as to allow storage of a pressure transmitting fluid; a pressing member that presses the sensing cuff toward the measurement target site and causes the sensing cuff to compress the measurement target site; and a fluid circuit that can be configured by switching among a supply mode of suppling the pressure transmitting fluid from the pump to the sensing cuff, a discharge mode of discharging the fluid from the sensing cuff to atmosphere, and a shut-off mode of shutting off fluid supply to the sensing cuff and fluid discharge from the sensing cuff, wherein, the method comprising, in the worn state:
executing first preparation processing that, with the fluid circuit switched to the discharge mode, operates the pressing member to press the sensing cuff toward the measurement target site and discharges a fluid remaining in the sensing cuff to the atmosphere through the fluid circuit;

executing second preparation processing that, with the fluid circuit switched to the supply mode after the first preparation processing, causes the sensing cuff to store a predetermined amount of the pressure transmitting fluid received from the pump through the fluid circuit; and executing measurement processing that, with the fluid circuit switched to the shut-off mode after the second preparation processing, operates the pressing member to press the sensing cuff toward the measurement target site and causes the sensing cuff to compress the measurement target site, and meanwhile, calculates a blood pressure of the measurement target site based on a pressure of the pressure transmitting fluid stored in the sensing cuff by an oscillometric method.

In the blood pressure measurement method of the present disclosure, the following processing is performed in the worn state of the belt being worn around the measurement target site. That is, with the fluid circuit switched to the discharge mode, the pressing member is operated to press the sensing cuff, and the fluid remaining in the sensing cuff is discharged to the atmosphere through the fluid circuit (first preparation processing). As a result, even if the fluid remains in the sensing cuff after the blood pressure measurement by the sphygmomanometer and before the next blood pressure measurement, the fluid is discharged from the sensing cuff. Next, after the first preparation processing, with the fluid circuit switched to the supply mode, the sensing cuff is caused to store the predetermined amount of pressure transmitting fluid received from the pump through the fluid circuit (second preparation processing). As a result, the pressure transmitting fluid is stored in the sensing cuff. At this time, because the remaining fluid has been discharged from the sensing cuff by the first preparation processing, the amount of pressure transmitting fluid stored in the sensing cuff becomes constant. Next, after the second preparation processing, with the fluid circuit switched to the shut-off mode, the pressing member operates to press the sensing cuff and causes the sensing cuff to compress the measurement target site, and meanwhile, the blood pressure of the measurement target site is calculated based on the pressure of the pressure transmitting fluid stored in the sensing cuff by the oscillometric method (measurement processing). Thereby, for example, as disclosed in JP 2018-102868 A and JP 2018-102867 A, as a result of setting the width dimensions of the belt, the pressing member, and the sensing cuff (as appropriate, these are collectively referred to as a "cuff") to be small (for example, about 25 mm), the blood pressure of the measurement target site is calculated accurately even when the compression loss of the pressing member occurs during pressurization. In particular, as described above, because the amount of the pressure transmitting fluid stored in the sensing cuff becomes constant after the operation of the second preparation processing unit, the blood pressure is calculated accurately.

In yet another aspect, a computer-readable recording medium storing a program according to the present disclosure is a computer-readable recording medium non-transitorily storing a program for causing a computer to execute the above blood pressure measurement method.

By making a computer read the program stored in the computer-readable recording medium according to the present disclosure and causing the computer to execute the program, the above blood pressure measurement method can be implemented.

As is clear from the above, according to the sphygmomanometer and the blood pressure measurement method of the present disclosure, it becomes possible to create, before measuring a blood pressure, a state for making a blood pressure measurement accurate. In addition, by making a computer read the program stored in the computer-readable recording medium according to the present disclosure and causing the computer to execute the program, the above blood pressure measurement method can be implemented.

The above embodiments are illustrative, and are modifiable in a variety of ways without departing from the scope of this invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A sphygmomanometer comprising:
a main body mounted with a pump;
a belt extending from the main body and configured to be worn around a measurement target site;
a bag-shaped sensing cuff configured to be arranged, in a worn state of the belt being worn around the measurement target site, at a portion of an inner circumferential side of the belt that crosses an artery passing portion of the measurement target site, and configured to store a first fluid for pressure transmitting;
a pressing member configured, in the worn state, to press the sensing cuff toward the measurement target site and cause the sensing cuff to compress the measurement target site;
a fluid circuit configured to switch among
a supply mode of supplying the first fluid from the pump to the sensing cuff by opening a first valve and closing a second valve,
a discharge mode of discharging the first fluid from the sensing cuff to atmosphere by opening the second valve and closing the first valve, and
a shut-off mode of shutting off (i) the supplying of the first fluid to the sensing cuff and (ii) the discharging of the first fluid from the sensing cuff by closing the first and second valves; and
a processor, the processor being configured to execute, in the worn state:
first preparation processing, with the fluid circuit switched to the discharge mode, to operate the pressing member to press the sensing cuff toward the measurement target site and to discharge the first fluid remaining in the sensing cuff to the atmosphere through the fluid circuit;
second preparation processing, with the fluid circuit switched to the supply mode following the first preparation processing, to cause the sensing cuff to store a predetermined amount of the first fluid received from the pump through the fluid circuit; and
measurement processing to, with the fluid circuit switched to the shut-off mode after the second preparation processing,
operate the pressing member to press the sensing cuff toward the measurement target site and causing the sensing cuff to compress the measurement target site, and
calculate a blood pressure of the measurement target site based on a pressure of the first fluid stored in the sensing cuff by an oscillometric method.

2. The sphygmomanometer according to claim 1, wherein the pressing member includes a bag-shaped pressing cuff and arranged between the belt and the sensing cuff, and under control of the processor,
when the pressing member is being operated, the fluid circuit supplies a second fluid for pressurizing from the pump to the pressing cuff to expand the pressing cuff and causes the sensing cuff to press toward the measurement target site, and
when the pressing member is not operating, the fluid circuit discharges the second fluid to the atmosphere from the pressing cuff.

3. The sphygmomanometer according to claim 1, wherein the pressing member includes a bag-shaped pressing cuff arranged at a portion of the inner circumferential side of the belt that becomes opposite to the sensing cuff in the worn state, and
under control of the processor,
when the pressing member is being operated, the fluid circuit supplies a second fluid for pressurizing from the pump to the pressing cuff to expand the pressing cuff and causes the sensing cuff to press toward the measurement target site, and
when the pressing member is not operating, the fluid circuit discharges the second fluid to the atmosphere from the pressing cuff.

4. The sphygmomanometer according to claim 2, wherein the processor is further configured to execute, with the fluid circuit switched to the shut-off mode following the second preparation processing, a third preparation processing of deactivating the pressing member and discharging the second fluid from the pressing cuff to the atmosphere to remove a pressing applied to the sensing cuff, such that the first fluid stored in the sensing cuff by the second preparation processing is distributed inside the sensing cuff, and
the measurement processing is executed following the third preparation processing with the shut-off mode of the fluid circuit maintained.

5. The sphygmomanometer according to claim 2, further comprising
a pressing cuff pressure sensor configured to measure pressure in the pressing cuff.

6. The sphygmomanometer according to claim 1, further comprising
a sensing cuff pressure sensor configured to measure pressure in the sensing cuff.

7. The sphygmomanometer according to claim 1, wherein the main body is arranged at a portion opposite to the sensing cuff in a circumferential direction of the belt.

8. A blood pressure measurement method that uses a sphygmomanometer comprising: a main body mounted with a pump; a belt extending from the main body and configured to be worn around a measurement target site; a bag-shaped sensing cuff configured to be arranged, in a worn state of the belt being worn around the measurement target site, at a portion of an inner circumferential side of the belt that crosses an artery passing portion of the measurement target site, and configured to store a first fluid for pressure transmitting; a pressing member configured, in the worn state, to press the sensing cuff toward the measurement target site and cause the sensing cuff to compress the measurement target site; and a fluid circuit configured to switch among a supply mode of supplying the first fluid from the pump to the sensing cuff by opening a first valve and closing a second valve, a discharge mode of discharging the first fluid from the sensing cuff to atmosphere by opening the second valve and closing the first valve, and a shut-off mode of shutting off (i) the supplying of the first fluid to the sensing cuff and (ii) the discharging of the first fluid from the sensing cuff by closing the first and second valves, the method comprising, in the worn state:
- executing a first preparation processing, with the fluid circuit switched to the discharge mode, to operate the pressing member to press the sensing cuff toward the measurement target site and discharging the first fluid remaining in the sensing cuff to the atmosphere through the fluid circuit;
- executing a second preparation processing, with the fluid circuit switched to the supply mode following the first preparation processing, to cause the sensing cuff to store a predetermined amount of the first fluid received from the pump through the fluid circuit; and
- executing a measurement processing to, with the fluid circuit switched to the shut-off mode after the second preparation processing,
  - operate the pressing member to press the sensing cuff toward the measurement target site and cause the sensing cuff to compress the measurement target site, and
  - calculate a blood pressure of the measurement target site based on a pressure of the first fluid stored in the sensing cuff by an oscillometric method.

9. A non-transitory computer-readable recording medium storing a program configured to cause a computer to execute the blood pressure measurement method according to claim 8.

10. The sphygmomanometer according to claim 3, wherein
the processor is further configured to execute, with the fluid circuit switched to the shut-off mode following the second preparation processing, a third preparation processing of deactivating the pressing member and discharging the second fluid from the pressing cuff to the atmosphere to remove a pressing applied to the sensing cuff, such that the first fluid stored in the sensing cuff by the second preparation processing is distributed inside the sensing cuff, and
the measurement processing is executed following the third preparation processing with the shut-off mode of the fluid circuit maintained.

11. The sphygmomanometer according to claim 3, further comprising
a pressing cuff pressure sensor configured to measure pressure in the pressing cuff.

12. A sphygmomanometer comprising:
a main body mounted with a pump;
a belt extending from the main body and configured to be worn around a measurement target site;
a bag-shaped sensing cuff configured to be arranged, in a worn state of the belt being worn around the measurement target site, at a portion of an inner circumferential side of the belt that crosses an artery passing portion of the measurement target site, and configured to store a first fluid for pressure transmitting;
a pressing member configured, in the worn state, to press the sensing cuff toward the measurement target site and to cause the sensing cuff to compress the measurement target site;
a fluid circuit configured to switch among
  - a supply mode of supplying the first fluid from the pump to the sensing cuff by opening a first valve and closing a second valve,
  - a discharge mode of discharging the first fluid from the sensing cuff to atmosphere by opening the second valve and closing the first valve, and
  - a shut-off mode of shutting off (i) the supplying of the first fluid to the sensing cuff and (ii) the discharging of the first fluid from the sensing cuff by closing the first and second valves; and
a processor, the processor being configured to execute, in the worn state:
  - first preparation processing, with the fluid circuit switched to the discharge mode, to operate the pressing member to press the sensing cuff toward the measurement target site and discharging the first fluid remaining in the sensing cuff to the atmosphere through the fluid circuit;
  - second preparation processing, with the fluid circuit switched to the supply mode following the first preparation processing, to cause the sensing cuff to store a predetermined amount of the first fluid received from the pump through the fluid circuit;
  - third preparation processing, with the fluid circuit switched to the shut-off mode following the second preparation processing, to deactivate the pressing member to remove a pressing applied to the sensing cuff, such that the first fluid stored in the sensing cuff by the second preparation processing is distributed inside the sensing cuff, and
  - measurement processing to, with the shut-off mode of the fluid circuit maintained following the third preparation processing,
    - operate the pressing member to press the sensing cuff toward the measurement target site and causing the sensing cuff to compress the measurement target site, and
    - calculate a blood pressure of the measurement target site based on a pressure of the first fluid stored in the sensing cuff by an oscillometric method.

* * * * *